United States Patent
Chen et al.

(10) Patent No.: US 6,519,534 B2
(45) Date of Patent: *Feb. 11, 2003

(54) PAPER WEB BREAKAGE PREDICTION USING BOOTSTRAP AGGREGATION OF CLASSIFICATION AND REGRESSION TREES

(75) Inventors: Yu-To Chen, Pleasanton, CA (US); Piero Patrone Bonissone, Schenectady, NY (US)

(73) Assignee: General Electric Company, Niskayuna, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/929,536

(22) Filed: Aug. 13, 2001

(65) Prior Publication Data

US 2002/0052699 A1 May 2, 2002

Related U.S. Application Data

(63) Continuation-in-part of application No. 09/583,154, filed on May 30, 2000.

(51) Int. Cl.[7] ............................................. G01B 5/30
(52) U.S. Cl. ...................... 702/34; 73/865.8; 702/182
(58) Field of Search ........................... 702/34, 182, 35, 702/36, 85, 115, 183, 184; 162/263; 73/598, 606, 649, 767, 794, 865.8; 34/117, 445; 700/78, 79, 80, 83

(56) References Cited

U.S. PATENT DOCUMENTS

| | | | | |
|---|---|---|---|---|
| 5,013,403 A | * | 5/1991 | Chase | 162/198 |
| 5,104,488 A | * | 4/1992 | Chase | 162/198 |
| 5,314,581 A | * | 5/1994 | Lin et al. | 162/263 |
| 5,884,415 A | * | 3/1999 | Sims et al. | 34/117 |
| 6,319,362 B1 | * | 11/2001 | Huhtelin et al. | 162/190 |

* cited by examiner

Primary Examiner—Marc S. Hoff
Assistant Examiner—Edward Raymond
(74) Attorney, Agent, or Firm—David C. Goldman; Noreen C. Johnson

(57) ABSTRACT

System and method for predicting web breaks in a paper machine. Principal components analysis and an aggregated classification and regression tree (CART) model are used to predict web break sensitivity from measurements taken from a paper mill where the paper machine is located.

50 Claims, 20 Drawing Sheets

PAPER WEB BREAKAGE PREDICTION USING BOOTSTRAP AGGREGATION OF CLASSIFICATION AND REGRESSION TREES

This is a continuation-in-part of Ser. No. 09/583,154 filed May 30, 2000.

BACKGROUND OF THE INVENTION

This invention relates generally to a paper mill, and more particularly, to a system and method for predicting web break sensitivity in a paper machine and isolating machine variables affecting the predicted web break sensitivity according to data obtained from the paper mill.

A paper mill is a highly complex industrial facility that comprises a multitude of equipment and processes. In a typical paper mill there is an area for receiving raw material used to make the paper. The raw material generally comprises wood in the form of logs that are soaked in water and tumbled in slatted metal drums to remove the bark. The debarked logs are then fed into a chipper, a device with a rotating steel blade that cuts the wood into pieces about ⅛" thick and ½" square. The wood chips are then stored in a pile. A conveyor carries the wood chips from the pile to a digester, which removes lignin and other components of the wood from the cellulose fibers, which will be used to make paper. In particular, the digester receives the chips and mixes them with cooking chemicals, which are called "white liquor". As the chips and liquor move down through the digester, the lignin and other components are dissolved, and the cellulose fibers are released as pulp. At the bottom of the digester, the pulp is rinsed, and the spent chemicals known as "black liquor" are separated and recycled.

Next, the pulp is cleaned for a first time and then screened. Uncooked knots and wood chips, which cannot be passed through the screen, are returned to the digester to be cooked again. As for the screened pulp, it is cleaned a second time to obtain a virgin, unbleached pulp. The effluent from the second cleaning is then used for screening, and goes back to the first cleaning station before it is used in the digester. The used water ends its journey in a waste water primary treatment unit located in another location within the paper mill.

At this point, the pulp is free of lignin, but is too dark to use for most grades of paper. The next step is therefore to bleach the pulp by treating it with chlorine, chlorine dioxide, ozone, peroxide, or any of several other treatments. A typical paper mill uses multiple stages of bleaching, often with different treatments in each step, to produce a bright white pulp. Next, refiners, vessels with a series of rotating serrated metal disks, are used to beat the pulp for various lengths of time depending on its origin and the type of paper product that will be made from it. Basically, the refiners serve to improve drainability. Next, a blender and circulator mix the pulp with additives and distribute the mix of papermaking fibers to a paper machine.

The paper machine generally comprises a wet-end section, a press section, and a dry-end section. At the wet-end section, the papermaking fibers are uniformly distributed onto a moving forming wire. The moving wire forms the fibers into a sheet and enables pulp furnish to drain by gravity and dewater by suction. The sheet enters the press section and is conveyed through a series of presses where additional water is removed and the web is consolidated (i.e., the fibers are forced into more intimate contact). At the dry-end section, most of the remaining water in the web is evaporated and fiber bonding develops as the paper contacts a series of steam-heated cylinders. The web is then pressed between metal rolls to reduce thickness and smooth the surface and wound onto a reel.

A problem associated with this type of paper machine is that the paper web is prone to break at both the wet-end section of the machine and at the dry-end section. Web breaks at the wet-end section, which typically occur at or near the site of its center roll, occur more often than breaks at the dry-end section. Dry-end breaks are relatively better understood, while wet-end breaks are harder to explain in terms of causes and are harder to predict and/or control. Web breaks at the wet-end section can occur as much 15 times in a single day. Typically, for a fully-operational paper machine there may be as much as 35 web breaks at the wet-end section of the paper machine in a month. The average production time lost as a result of these web breaks is about 1.6 hours per day. Considering that each paper machine operates continuously 24 hours a day, 365 days a year, the downtime associated with the web breaks translates to about 6.66% of the paper machine's annual production, which results in a significant reduction in revenue to a paper manufacturer. Therefore, there is a need to reduce the amount of web breaks occurring in the paper machine, especially at the wet-end section.

BRIEF SUMMARY OF THE INVENTION

This invention has developed a system and method for predicting web breaks in either the wet-end section or the dry-end section of the paper machine using a variety of data obtained from the paper mill. Thus, in this invention, there is provided a paper mill database containing a plurality of measurements obtained from the paper mill. Each of the plurality of measurements relate to a paper machine variable. A processor processes each of the plurality of measurements into break sensitivity data. A break predictor comprising a bagged classification analysis and regression tree model, responsive to the processor, predicts a web break sensitivity within the paper machine from the plurality of processed measurements.

DETAILED DESCRIPTION OF THE INVENTION

Figure 1:
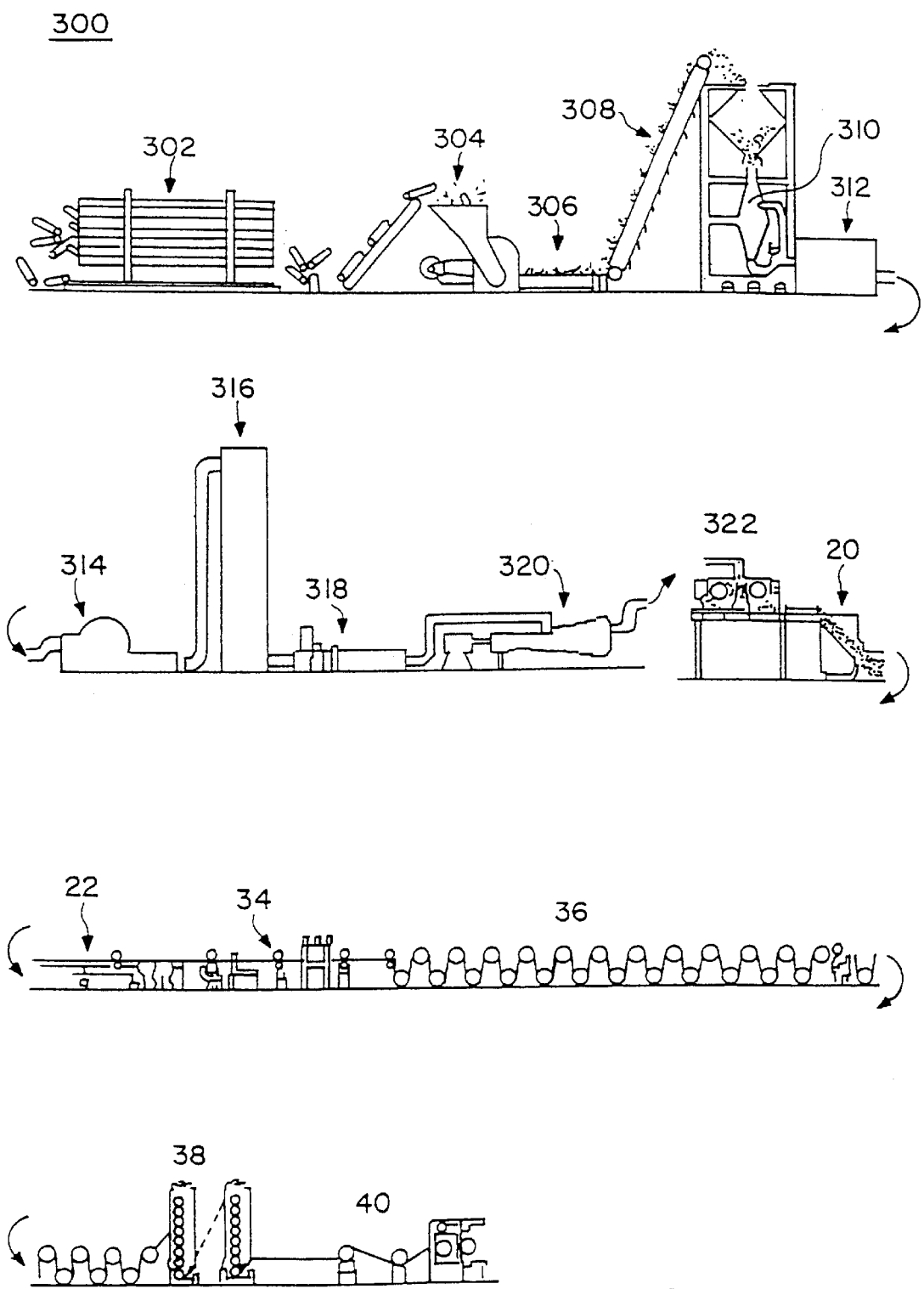
FIG. 1 shows a schematic diagram of a typical paper mill.

FIG. 1 shows a schematic diagram of a typical paper mill 300. In the paper mill 300, a debarker 302 receives logs that have been soaked in water and removes the bark from the logs using slatted metal drums. The debarked logs are then fed into a chipper 304, which cuts the log into small pieces of wood chips. The wood chips are then stored in a pile 306. A conveyor 308 carries the wood chips from the pile to a digester 310, which mixes the chips with the white liquor cooking chemicals. As the chips and liquor move down through the digester, lignin and other components are dissolved, and the cellulose fibers are released as pulp. The digester then empties the pulp into a blow pit 312. A washer 314 removes the pulp from the blow pit 312 and rinses it and separates and recycles the black liquor.

Next, the pulp is cleaned for a first time at a screening station (not shown). Uncooked knots and wood chips, which cannot pass through the screen, are returned to the digester for additional cooking. As for the screened pulp, it is cleaned a second time to obtain a virgin, unbleached pulp. A bleach tower 316 then receives the unbleached pulp and treats it with chemicals such as chlorine, chlorine dioxide, ozone, peroxide, etc., to produce a bright white pulp. Next, a beater 318 beats the pulp for a predetermined period of time and a refiner 320 then further refines the pulp. Next, a blender and circulator 322 mix the pulp with additives and distribute the mix of papermaking fibers to a paper machine. The paper machine comprises equipment such as a headbox 20, a wire 22, presses 34, dryers 36, calenders 38 and a reel 40, all of which are explained below in more detail. One of ordinary skill in the art will recognize that the paper mill 300 may have additional equipment and processes other than the ones shown in FIG. 1.

Figure 2:
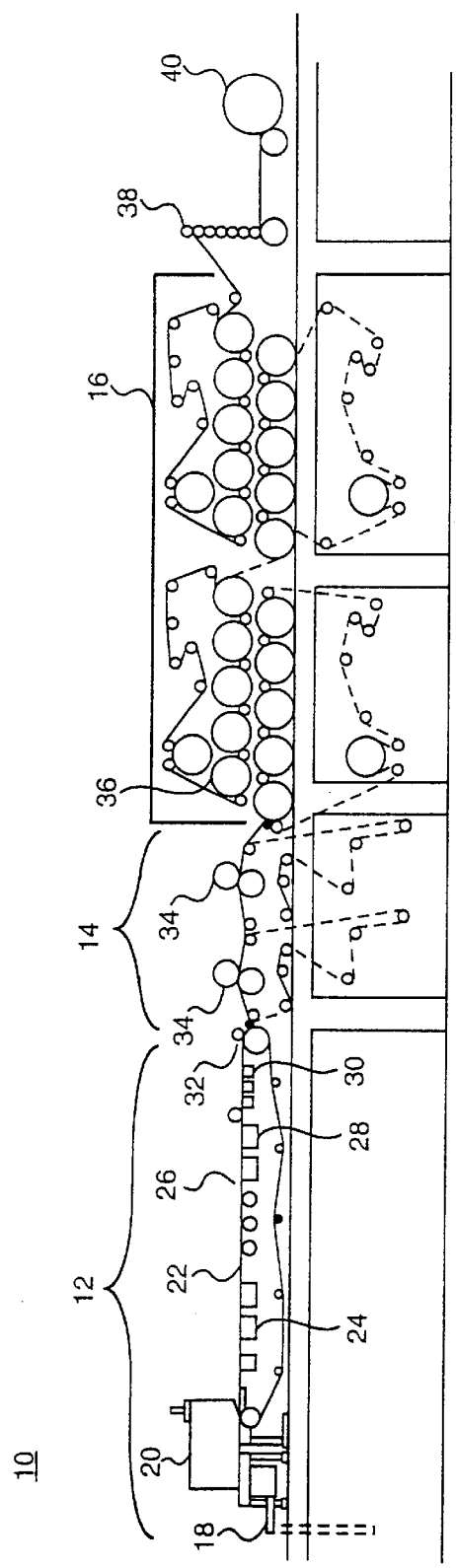
FIG. 2 shows a schematic diagram of a paper machine according to the prior art that is typically used in the paper mill shown in FIG. 1.

FIG. 2 shows a schematic diagram of a paper machine 10 according to the prior art that is typically used in the paper mill 300 shown in FIG. 1. The paper machine 10 comprises a wet-end section 12, a press section 14, and a dry-end section 16. At the wet-end section 12, a flowspreader 18 distributes papermaking fibers (i.e., a pulp furnish of fibers and filler slurry) uniformly across the machine from the back to the front. The papermaking fibers travel to a headbox 20 which is a pressurized flowbox. The pulp furnished is jetted from the headbox 20 onto a moving paper surface 22, which is an endless moving wire. The top section of the wire 22, referred to as the forming section, carries the pulp furnish. Underneath the forming section are many stationary drainage elements 24 which assist in drainage. As the wire 22 with pulp furnish travels across a series of hydrofoils or table rolls 26, white water drains from the pulp by gravity and pulsation forces generated by the drainage elements 24. Furnish consistency increases gradually and dewatering becomes more difficult as the wire 22 travels further downstream. Vacuum assisted hydrofoils 28 are used to sustain higher drainage and then high vacuum flat boxes 30 are used to remove as much water as possible. A suction couch roll 32 provides suction forces to improve water removal.

The sheet is then transferred from the wet-end section 12 to the press section 14 where the sheet is conveyed through a series of presses 34 where additional water is removed and the web is consolidated. In particular, the series of presses 34 force the fibers into intimate contact so that there is good fiber-to-fiber bonding. In addition, the presses 34 provide surface smoothness, reduce bulk, and promote higher wet web strength for good runnability in the dry-end section 16. At the dry-end section 16, most of the remaining water in the web is evaporated and fiber bonding develops as the paper contacts a series of steam-heated cylinders 36. The cylinders 36 are referred to as dryer drums or cans. The dryer cans 36 are mounted in two horizontal rows such that the web can be wrapped around one in the top row and then around one in the bottom row. The web travels back and forth between the two rows of dryers until it is dry. After the web has been dried, the web is transferred to a calendar section 38 where it is pressed between metal rolls to reduce thickness and smooth the surface. The web is then wound onto a reel 40.

Figure 3:
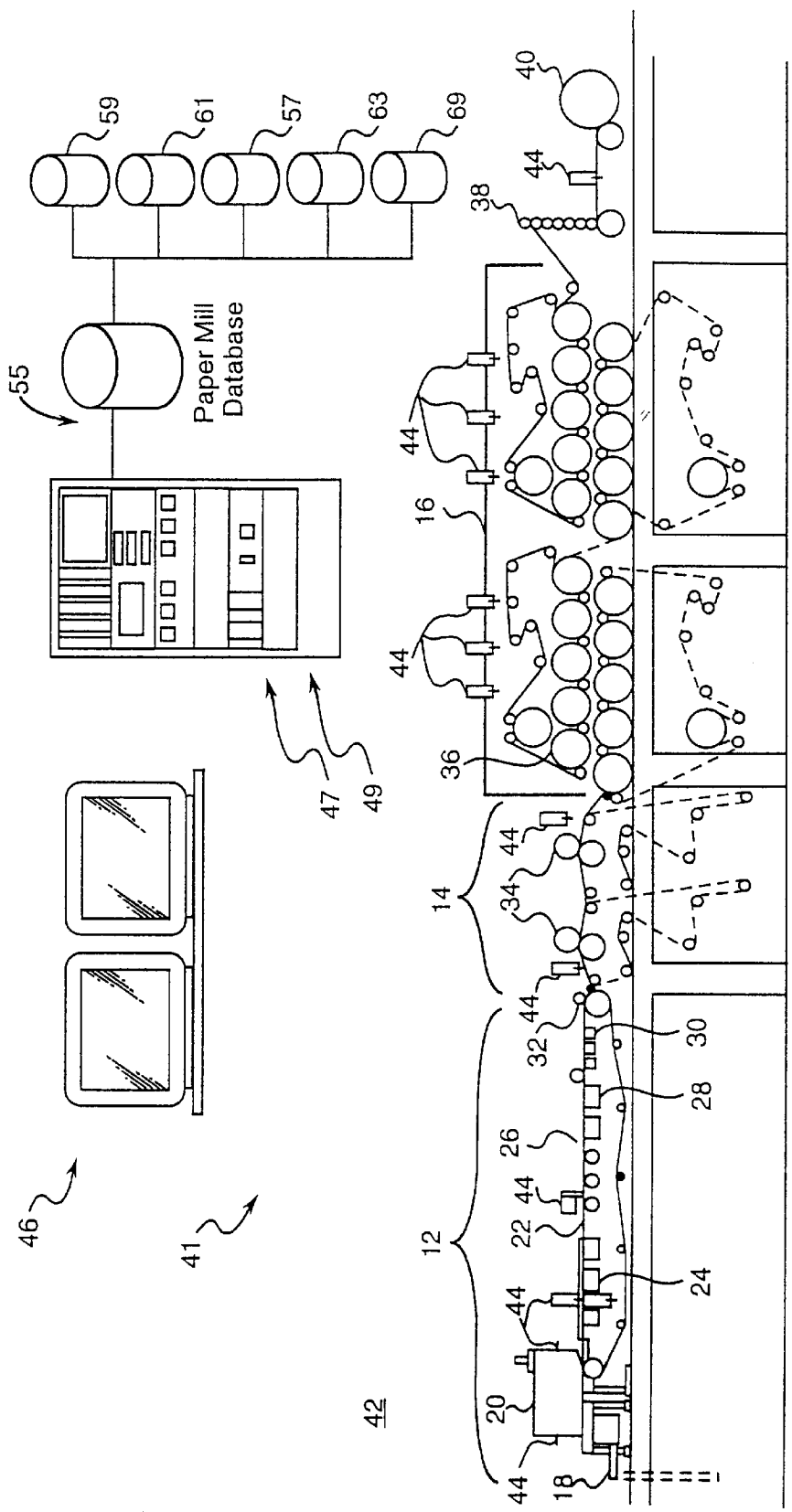
FIG. 3 shows a schematic of a paper machine used with this invention.

As mentioned earlier, the conventional paper machine is plagued with the paper web breaks at both the wet-end section of the machine and at the dry-end section. FIG. 3 shows a schematic of a system 41 that is capable of predicting paper web breaks and isolating the root causes for the breaks from data obtained throughout the paper mill 300 with which the paper machine operates. In addition to elements described with respect to FIG. 2, the paper machine 42 comprises a plurality of sensors 44 for obtaining various measurements throughout wet-end section 12, the press section 14, and the dry-end section 16. There are hundreds of different types of sensors (e.g., thermocouples, conductivity sensors, flow rate sensors) located throughout the paper machine 42. For example, the re may be as many as 374 sensors located throughout the wet-section of the paper machine 42. For ease of illustration, the sensors 44 are shown in FIG. 3 as substantially the same symbol even though there are many different types of sensors used that are typically designated by different configurations. Each sensor 44 obtains a different measurement that relates to a paper machine variable. Some examples of the type of measurements that may be taken are chemical pulp feed, wire speed, wire pit temperature, wire water pH, and ash content. Note that these measurements are only possible examples of some of the measurements obtained by the sensors 44 and this invention is not limited thereto.

A computer 46, coupled to the paper machine 42, receives each of the measurements obtained from the sensors 44. The computer 46 stores the measurements in a paper mill database 55, which places the measurements in a paper machine database 57. The paper mill database 55 also comprises other databases such as a raw materials database 59, a preprocess database 61, an operator shift database 63 and a maintenance schedule database 69. The raw materials database 59 stores data on the raw materials used to make the paper that include but are not limited to TMP, kraft, raw broke, coated broke, chemicals. The preprocess database 61 stores data measured during the preprocessing stages of the raw material such as the screening, cleaning, refining, blending, etc. Some of the preprocess data includes, but are not limited to solution Ph, percentages of raw materials, etc. The data in the operator shift database 63 stores data that occurs during the different shifts of operation of the paper machine such as hours since the time of the last shift change. The maintenance schedule database 69 stores data on the maintenance performed on the paper machine (e.g., hours of operations since last blade change). All of the data in these databases are inputted automatically or manually using well known methods. Furthermore, the paper mill database 55 is not limited to these specific databases and can include other databases that store data obtained from any of the equipment and processes located within the paper mill 300.

Figure 4:
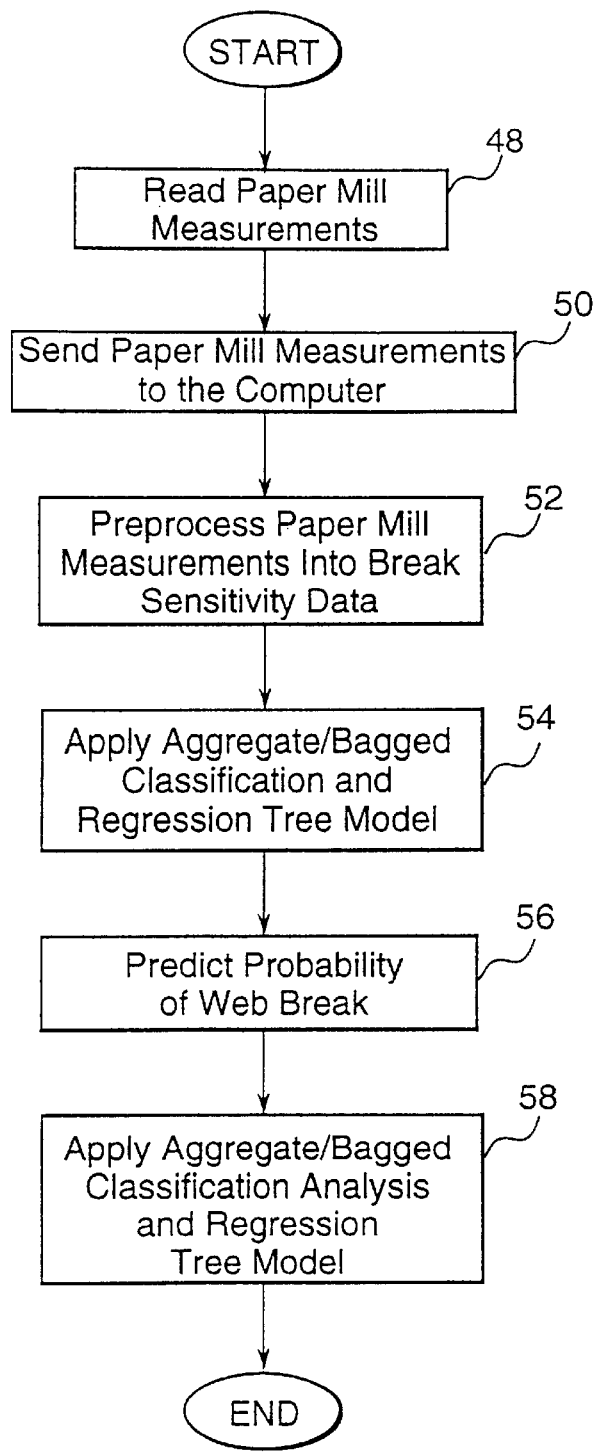
FIG. 4 is a flow chart setting forth the steps used in this invention to predict a web break in a paper machine.

The computer 46 preprocesses selected ones of the measurements stored in the paper mill database 55 and analyzes the preprocessed measurements according to a software-based predictive model 47 stored within the computer memory to determine a break sensitivity indicator which may be displayed by the computer. FIG. 4 is a flow chart setting forth the steps used by the computer in this invention to predict the web break sensitivity in the wet-end section of the paper machine 42 after the predictive model is sufficiently trained and tested. In FIG.. 4, the paper mill measurements are read at 48. Each of the readings relate to a paper machine variable determined to affect web breakage sensitivity. After obtaining the readings, the measurements are sent to the computer 46 at 50. The computer then preprocesses the measurements into a break sensitivity data set at 52. In particular, in one preferred embodiment, the measurements are processed to determine a value for a principal component, its first derivative, second derivative and difference from steady-state. The preferred variable selection and preprocessing techniques are described below in more detail. After preprocessing, the computer 46 applies a predictive model to the preprocessed measurements at 54. In particular, the computer 46 uses an aggregated inductive reasoning tool, such as an aggregated classification and regression tree (CART) model, to predict the break sensitivity of the paper web based on the readings. The aggregated CART model is preferably generated using bootstrap aggregation, also known as bagging, which samples the training data with replacement to generate the predictive model. The generated break sensitivity prediction indicates a high or low web break probability at 56. The prediction of the high or low probability of a web break within the paper machine is indicated by a "Break" or "Non-break" status, respectively, which may be displayed to the operator of the machine. The aggregated CART model and the derived rules are described below in more detail. Thus, the aggregated CART model can be used as a diagnostic tool to indicate changes in the paper web break sensitivity to allow the operator to take corrective action to reduce the probability of a web break.

Figure 5:
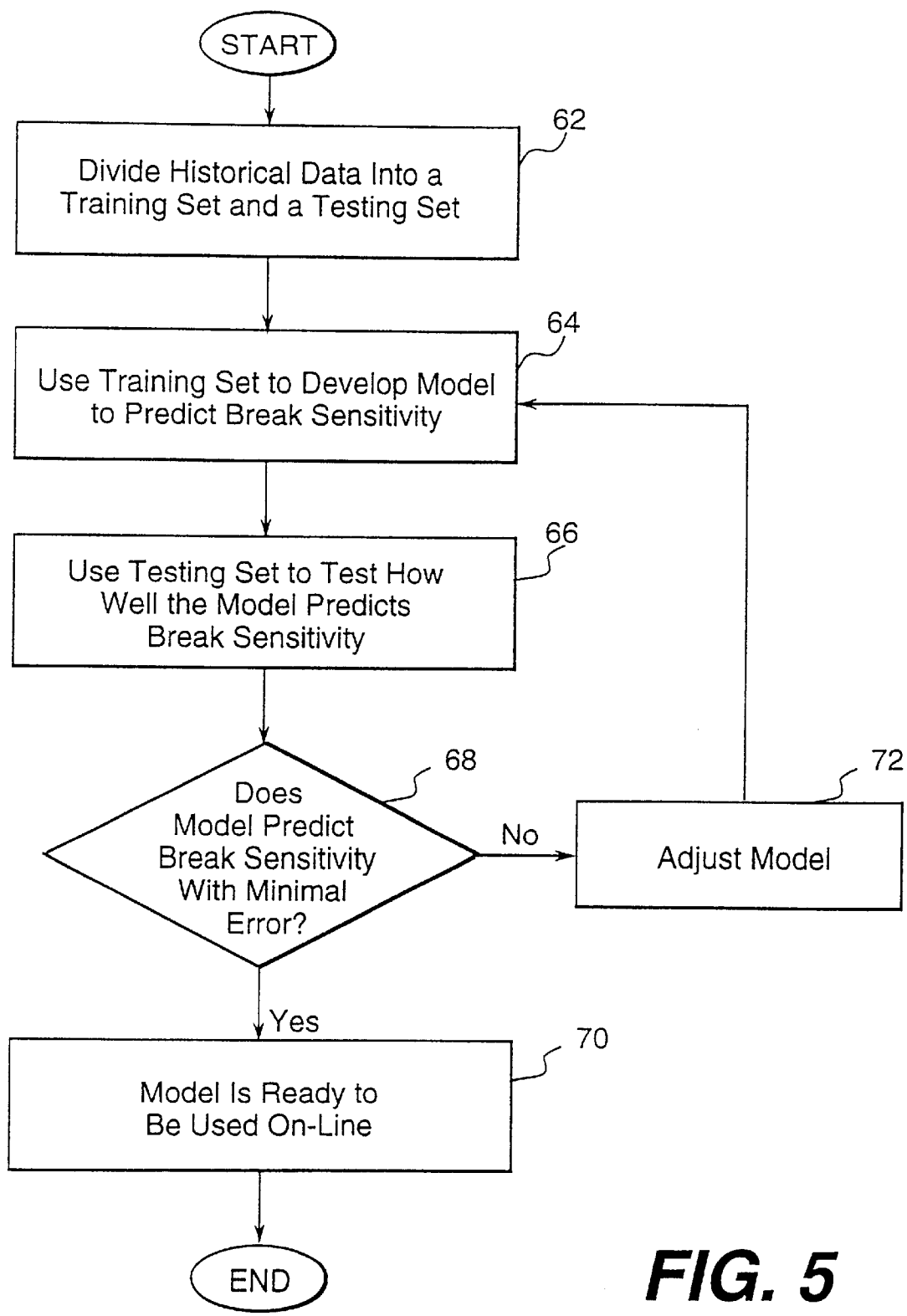
FIG. 5 is a flow chart setting forth the steps used to train and test the predictive model in this invention.

In order for this invention to be able to predict web break sensitivity, the computer 46 containing the CART model is trained and tested with historical web break data. For example, in one preferred embodiment, about 67% of the historical data is used for training and about 33% is used for testing. One skilled in the art will realize that these percentages may vary dramatically and still produce acceptable results. A flow chart describing the training and testing steps performed in this invention is set forth in FIG. 5. At 62, the historical data set is divided into two parts, a training set and a testing set. The training set is used to train the model to predict the web break tendency and the testing set is used to test the prediction performance of the model when presented with a new data set. If the training is successful, then the model is expected to do reasonably well for a data set that it has never seen before. At 64, the training set is used to train the model to predict the web break sensitivity. In this invention, the model is trained by using the process described below in detail. Once a model is developed from the training set, the testing set is utilized to test how well the trained model predicts the break sensitivity at 66. The testing is measured by using misclassification rates. If the trained model does predict the break sensitivity with minimal error (e.g., <about 20% misclassification) at 68, then the model is ready to be used on-line at 70 to predict the paper web break sensitivity. However, if the trained model is unable to predict the break tendency with minimal error at 68, then the model is adjusted at 72 and steps 64–68 are repeated until the misclassification rate error becomes small enough. For example, the model may be adjusted by returning to the preprocessing steps, discussed in detail below, and utilizing different filtering, smoothing and feature extraction algorithms.

Figure 6:
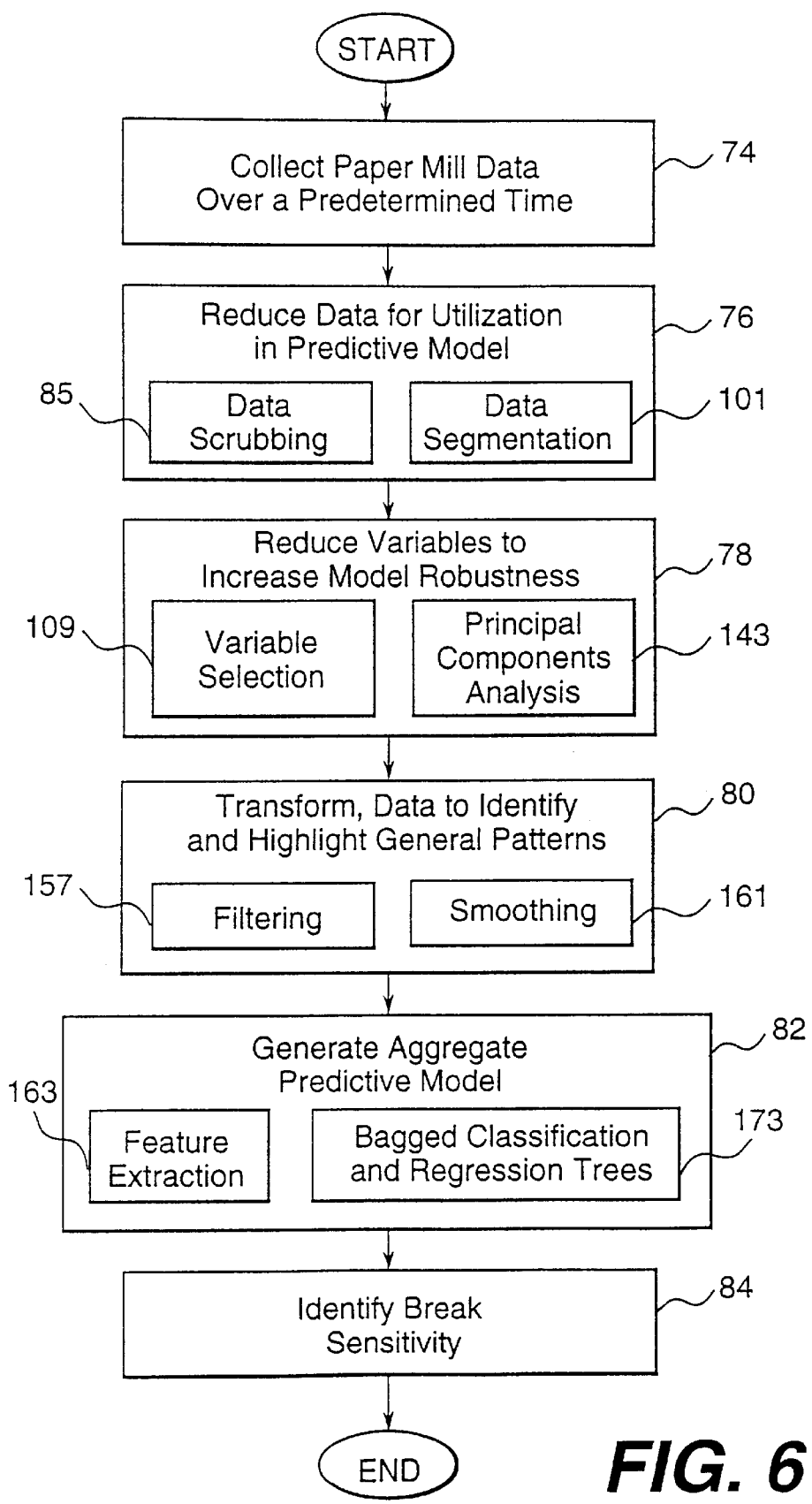
FIG. 6 is a flow chart setting forth the steps used in this invention to acquire historical web break data and preprocess the data.

FIG. 6 describes the historical web break data acquisition steps and the data preprocessing steps that are used in this invention for training. At 74, paper mill data, such as the data from the paper machine described in FIG. 3, are collected over a predetermined time period. In the preferred embodiment, data collection may focus on one area of the machine, such as the wet-end section. After the historical data has been collected, then a data reduction process is applied at 76 to render the historical data suitable for model building purposes. In the preferred embodiment, the data reduction is subdivided into a data scrubbing process at 85 and a data segmentation process at 101. Following the data reduction, a variable reduction technique is utilized at 78 in order to derive a simple, yet robust, predictive model. In the preferred embodiment, the variable reduction is subdivided into a variable selection process at 109 and a principal components analysis process at 143, as is discussed below in detail. Once the amount of data and the number of variables are reduced, then a value transformation is applied to the data at 80 to identify and highlight general patterns in the data that may be useful in predicting web break sensitivity. In the preferred embodiment, as is described below, the value transformation includes filtering techniques at 157 and smoothing techniques at 161. The transformed data is analyzed and used to generate a predictive model at 82. The predictive model determines a break sensitivity indicator at 84, which predicts a high or low break sensitivity. In a preferred embodiment, the model generation includes feature extraction techniques at 163 and CART techniques at 173, as are described below in detail.

The data gathering and model generation process will now be described in detail with reference to a preferred embodiment. Those skilled in the art will realize that the principles taught herein may be applied to other embodiments. As such, the present invention is not limited to this preferred embodiment. In one preferred embodiment, sensor data from 43 sensors located about the wet-end section of the paper machine are collected over about a twelve-month period. Note that this time period is illustrative of a preferred time period for collecting a sufficient amount of data and this invention is not limited thereto. Additional variables associated with the sensor measurements include two variables corresponding to date and time information and one variable indicating a web break. By using a sampling time of one minute, this data collection for 46 variables results in about 66,240 data points or observations during a 24-hour period of operation, and a very large data set over the twelve-month period.

Figure 7:
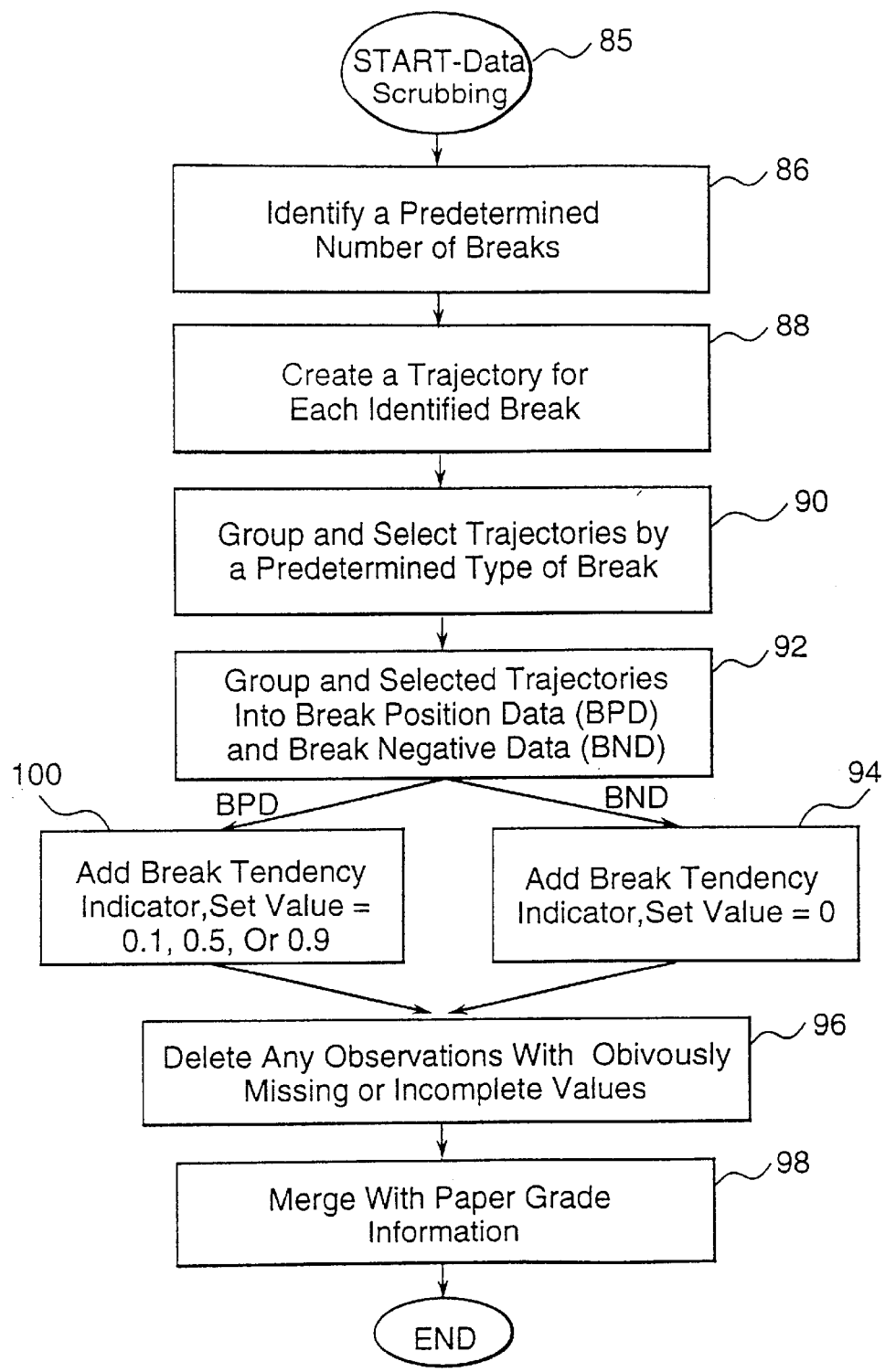
FIG. 7 is a flow chart setting forth the steps used in this invention to perform data scrubbing on the acquired historical data.

Referring to FIG. 7, for example, the data scrubbing portion 85 of the data reduction 76 (FIG. 6) involves grouping the data according to various break trajectories. A break trajectory is defined as a multivariate time-series starting at a normal operating condition and ending at a wet-end break. For example, a long break trajectory could last up to a couple of days, while a short break trajectory could be less than three hours long.

A predetermined number of web breaks are identified at 86. In the preferred embodiment, all of the web breaks are identified, although a smaller sample size may be used. For each web break, a trajectory of data is created over a predetermined window at 88. The size of the predetermined window may vary depending on the desired accuracy of the predictive model and on the typical length of the break trajectory data. For example, break trajectory windows of 1 hour to 1 day may be utilized, although preferred window sizes include 60, 120, 180 and 240 minutes. These trajectories are grouped by a predetermined type of break, and one of the groups may be 'selected for further processing at 90. For example, in the preferred embodiment there are four major groups of breaks, however, only breaks corresponding to situations defined as "unknown causes" are evaluated. The other major groups include breaks with known causes, where the problem is easier to solve and thus less attractive for predictive modeling. As a result, data relating to the known causes groups are taken out of the analysis. Thus, for example, the historical data can be reduced to 433 break trajectories, containing 443,273 observations and 46 variables.

Once the data relating to a selected group of trajectories, such as unknown causes, is defined, the selected break trajectory data is divided into a predetermined number of groups at 92. For example, the data may be divided into two groups to distinguish data associated with an imminent break from data associated with a stable operation. One skilled in the art will realize, however, that the data may be grouped in numerous other gradations in relation to the break. Utilizing two groups, the first group contains the set of observations taken within a predetermined pre-break to break time window, such as 60 minutes prior to the break to the moment of the break. This data set is denoted as break positive data and, in the preferred embodiment, contains 199,377 observations and 46 variables. The remaining data set, containing the set of observations greater than 60 minutes prior to the break, is denoted as break negative data. In the preferred embodiment, the break negative data contains 243,896 observations and 46 variables. The data collected after the moment of the break is discarded, since it is already known that the web has broken.

In the break negative data, a break tendency indicator variable is added to the data and assigned a value of 0 at 94. The break indicator value of 0 denotes that a break did not occur within the data set. Further, any incomplete observations and obviously missing values are deleted at 96.

Additionally, the break negative data is merged with data representing a paper grade variable at 98. For example, in a preferred embodiment, this yields a final set of break negative data containing 233,626 observations and 47 variables.

In the break positive data, a predetermined break sensitivity indicator variable is added to the data at 100. For example, using the 60 minute pre-break to break time window, the break sensitivity indicator is assigned a value of 0.1, 0.5 or 0.9, respectively, corresponding to the first, middle or last 20 minutes of the break trajectory. These break sensitivity indicator values represent a low, medium and high break possibility, respectively. As one skilled in the art will realize, the number and value of the break sensitivity indicators may vary based on the application. Further, any incomplete observations and obviously missing values are deleted at 96. Also, only the first data point corresponding to the break is included in the data set for each break trajectory. This allows each break trajectory data set to only include relevant data prior to the break. Additionally, the break positive data is merged with data representing a paper grade variable at 98. For example, this yields a final set of break positive data containing 26,453 observations and 47 variables. Thus, by performing data scrubbing, two data sets—break positive data and break negative data—are created and are used throughout the remainder of the process.

As one skilled in the art will realize, some of the common steps outlined above, such as deleting observations and merging paper grade information, may be performed in any order and prior to dividing the data sets into break positive and break negative data.

Figure 8:
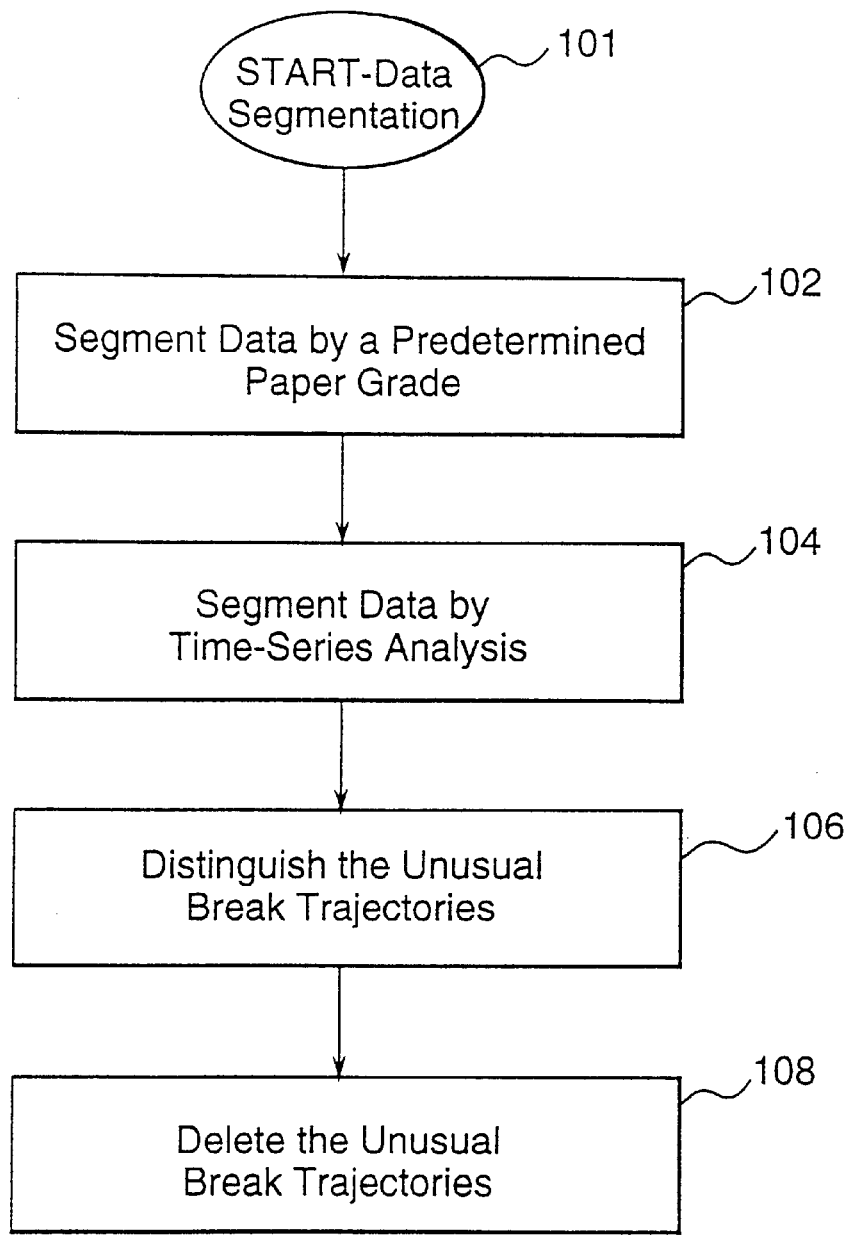
FIG. 8 is a flow chart setting forth the steps used in this invention to perform data segmentation on the acquired historical data.

After the data scrubbing 85, a data segmentation 101 is performed. Referring to FIG. 8, both the break positive and break negative data are segmented according to paper grade at 102, since different grades of paper may exhibit different break characteristics. In the preferred embodiment, for example, a paper grade denoted as RSV656 is selected and the break positive data originally containing 443 break trajectories and 26,453 observations (representing numerous paper grades) are segmented into 131 break trajectories and 7,348 observations relating to the RSV656 paper grade. Similarly, the break negative data containing 233,626 observations are segmented to 59,923 observations relating to the RSV656 paper grade.

The break, positive data are preferably further segmented by time-series analysis at 104. Because each break trajectory is a multivariate time-series containing a large amount of data, it is preferred to summarize each break trajectory by a single number to aid in the segmentation process. Before this analysis, however, a preliminary variable selection may be performed, including knowledge engineering, visualization and CART. As one skilled in the art will realize, the segmentation by time-series analysis and variable selection may be performed in any order. The variable selection process is described below in more detail. Although all of the readings could be used, in the preferred embodiment only 31 variables (out of 43 readings) are needed to distinguish the unusual trajectories. The unusual trajectories, which represent "outlier" trajectories that are significantly different than the majority of trajectories, are distinguished from the data set at 106 as a result of the time-series segmentation process. The following is a description of the algorithm for a preferred time-series segmentation process.

```
For each break trajectory
    • For each reading
        • Build an autoregressive model—AR(1.
    • End of "for" loop
    • (At this point, there are 31 AR(1) models; hence 31
      correspoding coefficients.
    • Compute the geometric mean of the 31 AR(1) coefficients.
End of "for" loop.
```

The autoregressive model for each reading is of order 1 according to the following equation: $x(t)=\alpha x(t-1)+\epsilon$; where $x(t)$=the reading indexed by time; $\alpha$=a coefficient relating the current reading to the reading from the previous time step; $x(t-1)$=the reading from the previous time step; and $\epsilon$=an error term. The idea is to summarize each multivariate time-series by a single number, which is the geometric mean of the individual univariate time-series of the break trajectory. Referring to FIG. 8, the geometric mean of AR(1) coefficients 103 for a representative plurality of break trajectories are shown in graphical form.

Figure 9:
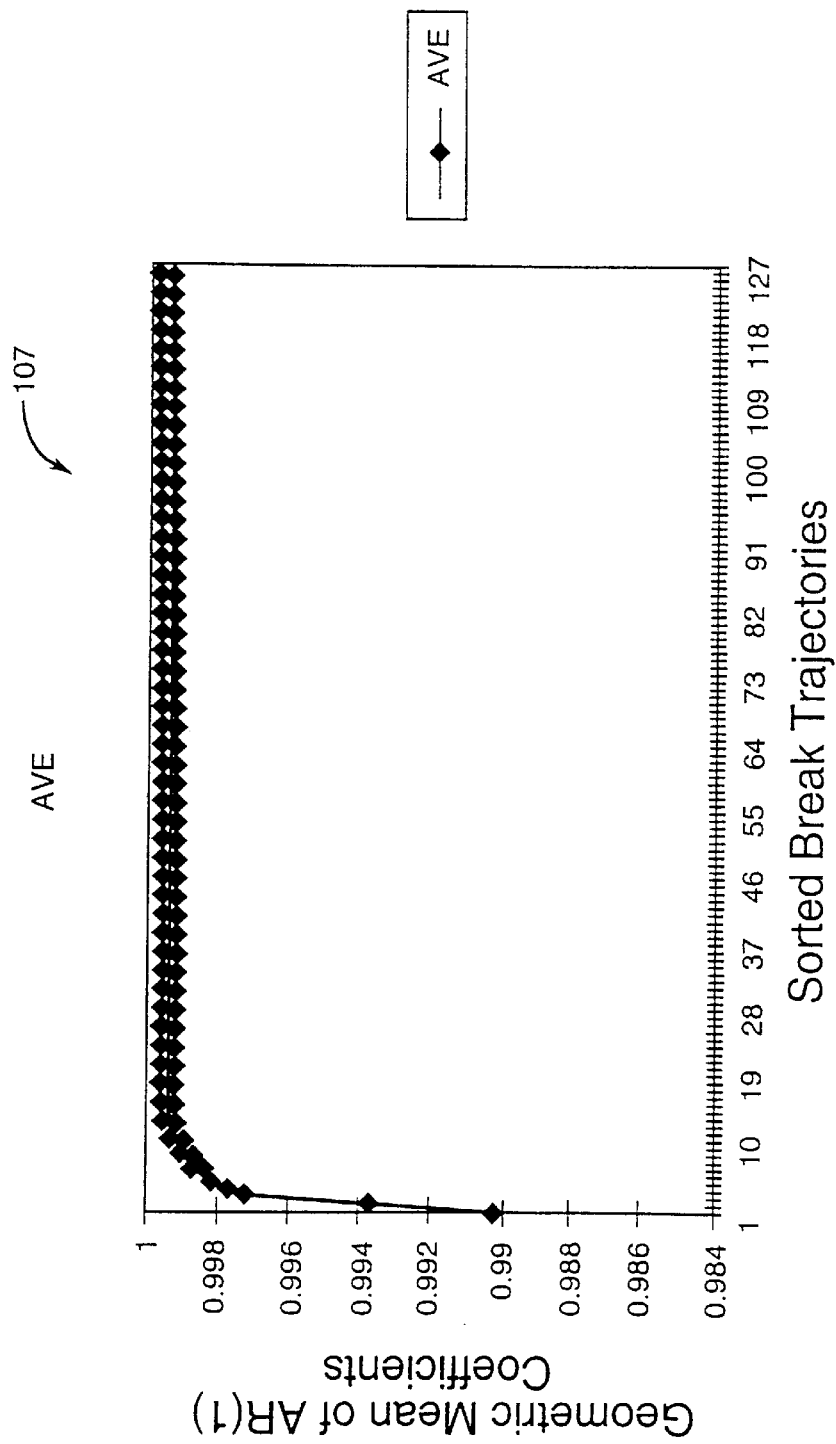
FIG. 9 is a graph for one preferred embodiment of the segmentation of the break positive data by time-series.

Once the break trajectories are summarized by a single number, they may be segmented into a predetermined number of groups in order to aid in modeling. For example, in a preferred embodiment, the break trajectories are divided into two groups. Referring to FIG. 9, one group consists of the first 11 break trajectories (the curved portion of the line) while the other group comprises the rest of the break trajectories. As one skilled in the art will realize, the number of predetermined groups and the point of division of the groups is a subjective decision that may vary from one data set to the next. In the preferred embodiment, for example, the first 11 break trajectories are all very fragmented. They correspond to an "avalanche of breaks," e.g., trajectories occurring one after another having lengths much shorter than 60 minutes (the one-hour time window that immediately follows a break), and therefore these unusual trajectories are removed from the data set used for model building at 108. Thus, for example, the data segmentation results in the break positive data for the RSV656 paper grade having 120 break trajectories and 6,999 observations.

Once the data reduction 76 (FIG. 6) has been completed, then a variable reduction process 78 (FIG. 6) is initiated to derive the simplest possible model to explain the past (training mode) and predict the future (testing mode). Typically, the complexity of a model increases in a nonlinear way with the number of inputs used by the model. High complexity models tend to be excellent in training mode, but rather brittle in testing mode. Usually, these high complexity models tend to overfit the training data and do not generalize well to new situations—referred to as "lack of model robustness." There is a modeling bias in favor of smaller models, thereby trading the potential ability to discover better fitting models in exchange for protection from overfitting. From the implementation point of view, the risk of more variables in the model is not limited to the danger of overfitting. It also involves the risk of more sensors malfunctioning and misleading the model predictions. In an academic setting, the risk/return tradeoff may be more tilted toward risk taking for higher potential accuracy in predicting future outcomes. Therefore, a reduction in the number of variables and its associated reduction of inputs is desired to derive simpler, more robust models.

Further, in the presence of noise it is desirable to use as few variables as possible, while predicting well. This is often referred to as the "principle of parsimonious." There may be combinations (linear or nonlinear) of variables that are actually irrelevant to the underlying process, that due to noise in data appear to increase the prediction accuracy. The idea is to use combinations of various techniques to select the variables with the greater discrimination power in break prediction.

Figure 10:
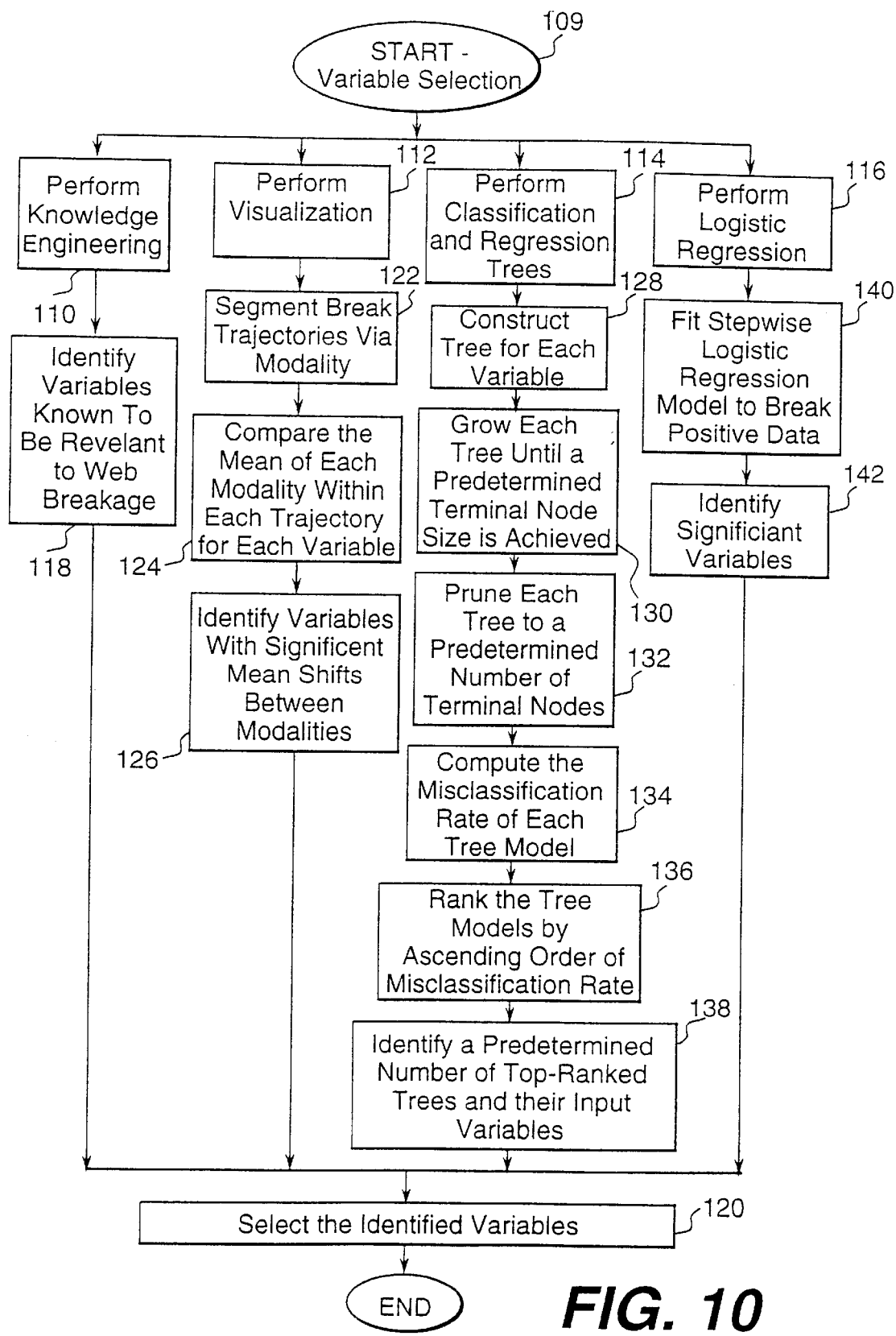
FIG. 10 is a flow chart setting forth the steps used in this invention to perform variable selection on the acquired historical data.

The variable reduction activity is subdivided into two steps, variable selection 109 and principal component analysis (PCA) 143, which are described below. Referring to FIG. 10, a number of techniques may be used for variable selection. They include performing knowledge engineering at 110, visualization at 112, CART at 114, logistic regression at 116, and other similar techniques. These techniques may be used individually, or preferably in combination, to select variables having greater discrimination power in predicting web breakage.

In the preferred embodiment, for example, by utilizing knowledge engineering all of the sensors relating to variables corresponding to paper stickiness and paper strength are identified at 118. In the preferred embodiment, it has been determined that paper stickiness and paper strength are important variables that affect web breakage. This results in selecting 16 readings and their associated variables at 120.

Figure 11:
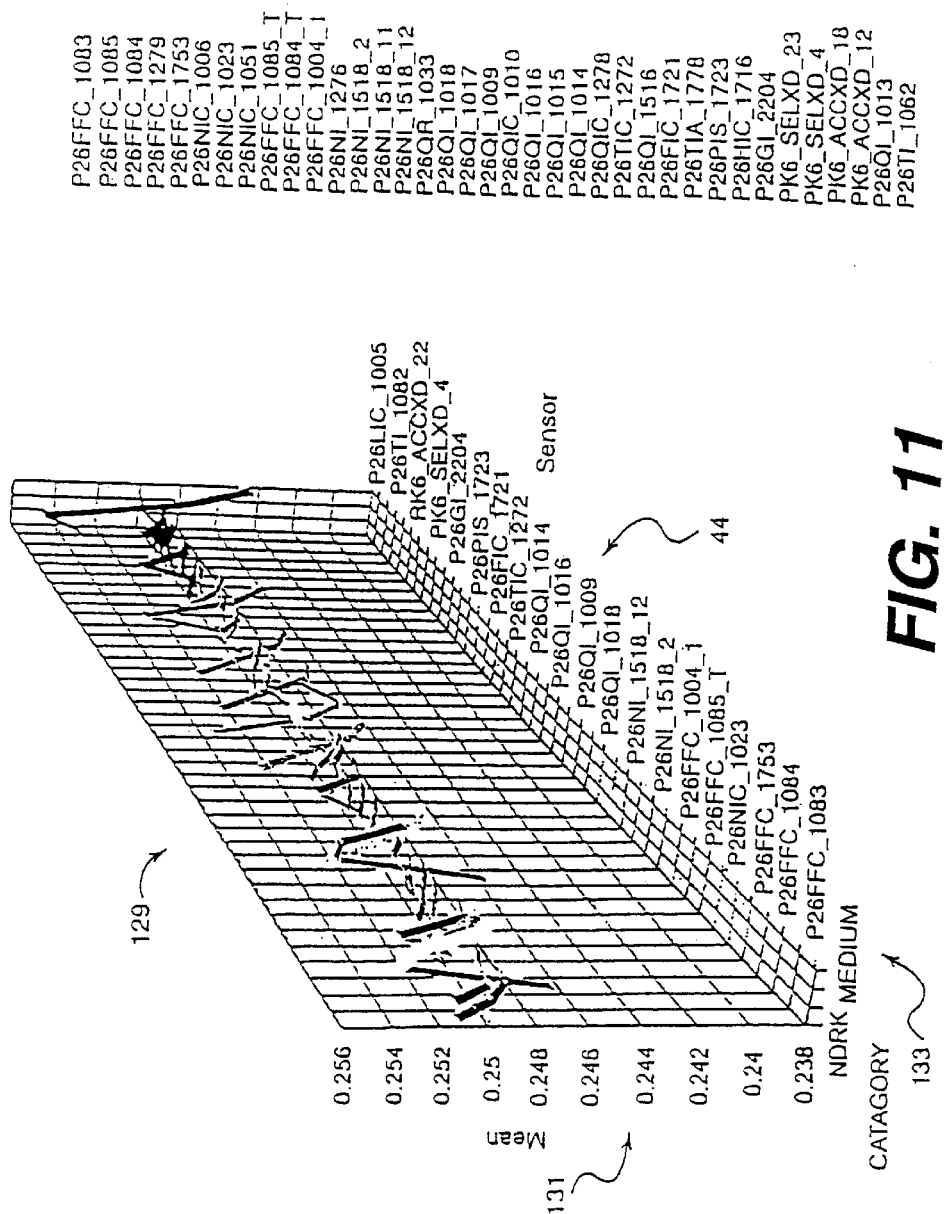
FIG. 11 is a graph for one preferred embodiment of variable selection by visualization of mean shift.

Visualization, for example, includes segmenting the break trajectories at 122 into four groups or modalities: break negative, break positive (low), break positive (medium) and break positive (high). The modalities of the break positive data correspond to the break tendency indicator variable of ad1, 0.5 and 0.9 discussed above. A comparison of the mean of each modality within each break trajectory is performed for each variable at 124. As a result, variables having significant mean shifts between modalities are identified and selected at 126 and 120. In the preferred embodiment, referring to FIG. 11, the visualization technique 129 plots the mean 131 for each reading 44 by modality 133, resulting in selecting another eight readings.

Further, in the preferred embodiment, another five readings are added utilizing CART. CART is used for variable selection as follows. Assume there are N input variables (the readings) and one output variable (the web break status, i.e. break or non-break). The following is an algorithm describing the variable selection process:

For each input variable:

Construct a tree model with the single input variable and the output variable at 128.

Let the tree grow until the size of each terminal node is no smaller than about 1/100 of the original data set at 130.

Prune the tree until the number of terminal nodes is around 10 at 132.

Compute the misclassification rate, which is the sum of the number of false positives and false negatives, of the tree model at 134.

End of "for" loop.

- (At this point, there are N tree models. Each tree has around 10 terminal nodes.)
- Rank the N tree models by ascending order of their misclassification rates at 136.
- Select the top 20 trees and their input variables at 138.

The basic idea is to use the misclassification rate as a measure of the discrimination power of each input variable, given the same size of tree for each input variable. As one skilled in the art will realize, the size of the tree, the pruning of the tree and selection of the top trees all include a predetermined number that may vary between applications, and this invention is not limited to the above-mentioned predetermined numbers. As a result of CART, five more variables not previously identified are selected at 120, making a total of 29 variables. As mentioned before, these 29 variables are used for time-series analysis based segmentation at 101 (FIGS. 6 and 8).

Another method to identify web break discriminating variables is logistic regression. For example, a stepwise logistic regression model may be fitted to the break positive data at 140. As a result, significant variables may be identified at 142 by examining variables included in the final logistic regression models. One skilled in the art will realize that other types of variable classification techniques may be utilized, such as multivariate adaptive regression splines ("MARS") and neural networks ("NN"). In the preferred embodiment, utilizing logistic regression results in a model that identifies two significant variables—"broke to broke screen" and "headbox ash consistency." Therefore, these variables are selected at 120 and the total number of variables is 31. A list of readings and variable selection methods, in one preferred embodiment, are set forth below in Table 1.

TABLE 1

Summary of variable selection.

| Variable ID | Reading ID | Meaning | −17 | Visualization | CART | Logistic Regression | Dropped | REASON TO DROP |
|---|---|---|---|---|---|---|---|---|
| s1 | P26FFC__1083 | TMP feed, flow | ✓ | | | | | |
| s2 | P26FFC__1085 | Chemical pulp feed | ✓ | | | | | |
| s3 | P26FFC__1084 | Broke feed | ✓ | | | | | |
| s4 | P26FIC__1279 | Filler to centrifugal cleaner pump | ✓ | | | | | |
| s5 | P27FFC__1753 | Clay flow | | ✓ | | | | |
| s6 | P26NIC__1051 | Broke to broke screen | | | | ✓ | | |
| s7 | P26FFC__1084_T | Broke percentage | | ✓ | | | | |
| s8 | P26FFC__1004__1 | Bleached TMP percentage | | | | | | |
| s9 | P26NI__1518__11 | Total retention | ✓ | | | | | |
| s10 | P26NI__1518__12 | Ash retention | ✓ | | | | | |
| s11 | P26QR__1033 | Chemical pulp freeness | ✓ | | | | | |
| s12 | P26QI__1018 | Chemical pulp pH | | | ✓ | | | |
| s13 | P26QI__1017 | Chemical pulp conductivity | | ✓ | | | | |
| s14 | P26QI__1016 | TMP conductivity | | ✓ | | | | |
| s15 | P26QI__1014 | Broke conductivity | | ✓ | | | | |
| s16 | P26QIC__1278 | Wire water pH | ✓ | | | | | |
| s17 | P26TIC__1272 | Wire pit temperature | ✓ | | | | | |
| s18 | P26QI__1516 | Headbox conductivity | ✓ | | | | | |
| s19 | P26FIC__1721 | Retention aid flow | ✓ | | | | | |
| s20 | P26TIA__1778 | Retention aid/dilution tank | | | ✓ | | | |
| s21 | P26HIC__1716 | Foam inhibitor flow to wair pits | | ✓ | | | | |
| s22 | P26GI__2204 | Slice lip position | ✓ | | | | | |
| s23 | PK6__SELXD__4 | Wire section speed | ✓ | | | | | |
| s24 | PK6__ACCXD__18 | Ash content | ✓ | | | | | |
| s25 | PK6__ACCXD__22 | K-moisture | ✓ | | | | | |
| s26 | P26QI__1013 | White water pH | | | ✓ | | | |
| s27 | P26TI__1062 | White water tower temperature | | | ✓ | | | |
| s28 | P26LIC__1005 | TMP proportioning chest | | | ✓ | | | |
| s29 | P26QIC__1240 | Air content (conrex) | | ✓ | | | | |
| s30 | P26NI__1518__2 | Headbox ash consistency | | | | ✓ | | |
| s31 | P26QI__1015 | Broke pH | | ✓ | | | | |
| s32 | P26FFC__1752 | Caoline flow | | | | | X | 2 |
| s33 | P26NIC__1006 | TMP feed, consistency | | | | | X | 3, 4 |
| s34 | P26NIC__1023 | Chemical pulp FEED, consistency | | | | | X | 3, 4 |
| s35 | P26FFC__1085_T | Chemical pulp percentage | | | | | X | 3, 4 |
| s36 | P26NI__1276 | Machine pulp | | | | | X | 3, 4 |

TABLE 1-continued

Summary of variable selection.

| Variable ID | Reading ID | Meaning | -17 | Visualization | CART | Logistic Regression | Dropped | REASON TO DROP |
|---|---|---|---|---|---|---|---|---|
| s37 | P26QI__1009 | TMP 1 tower pH | | | | | X | 3, 4 |
| s38 | P26QIC__1010 | TMP 2 tower pH | | | | | X | 3, 4 |
| s39 | P26PIS__1723 | retention aid pipe pressure before screens | | | | | X | 2 |
| s40 | P26F1__0221__1 | Outer wire, wire water | | | | | X | 1 |
| s41 | PK6__SELXD__23 | Draw difference 4th press - 1st drier-section | | | | | X | 3, 4 |
| s42 | TI3FFC__6068 | Alkaline feed | | | | | X | 2 |
| s43 | PK6__SELXD__22 | Draw difference 3rd - 4th press | | | | | X | 3, 4 |

For example, of the 43 potential readings, a total of 12 were dropped due to one or more of the reasons, corresponding to "Reason To Drop" in Table 1: 1- too many missing observations in paper grade RSV656 data; 2- too many missing observations; 3- misclassification rate is too high; and 4- the means among the low, medium and high groups are too close together.

The variables identified utilizing the variable selection techniques are then utilized for principal components analysis (PCA). PCA is concerned with explaining the variance-covariance structure through linear combinations of the original variables. PCA's general objectives are data reduction and data interpretation. Although p components are required to reproduce the total system variability, often much of this variability can be accounted for by a smaller number of the principal components (k<<p). In such a case, there is almost as much information in the first k components as there is in the original p variables. The k principal components can then replace the initial p variables, and the original data set, consisting of n measurements on p variables, is reduced to one consisting of n measurements on k principal components.

An analysis of principal components often reveals relationships that were not previously suspected and thereby allows interpretations that would not ordinarily result. Geometrically, this process corresponds to rotating the original p-dimensional space with a linear transformation, and then selecting only the first k dimensions of the new space. More specifically, the principal components transformation is a linear transformation, which uses input data statistics to define a rotation of original data in such a way that the new axes are orthogonal to each other and point in the direction of decreasing order of the variances. The transformed components are totally uncorrelated.

Figure 12:
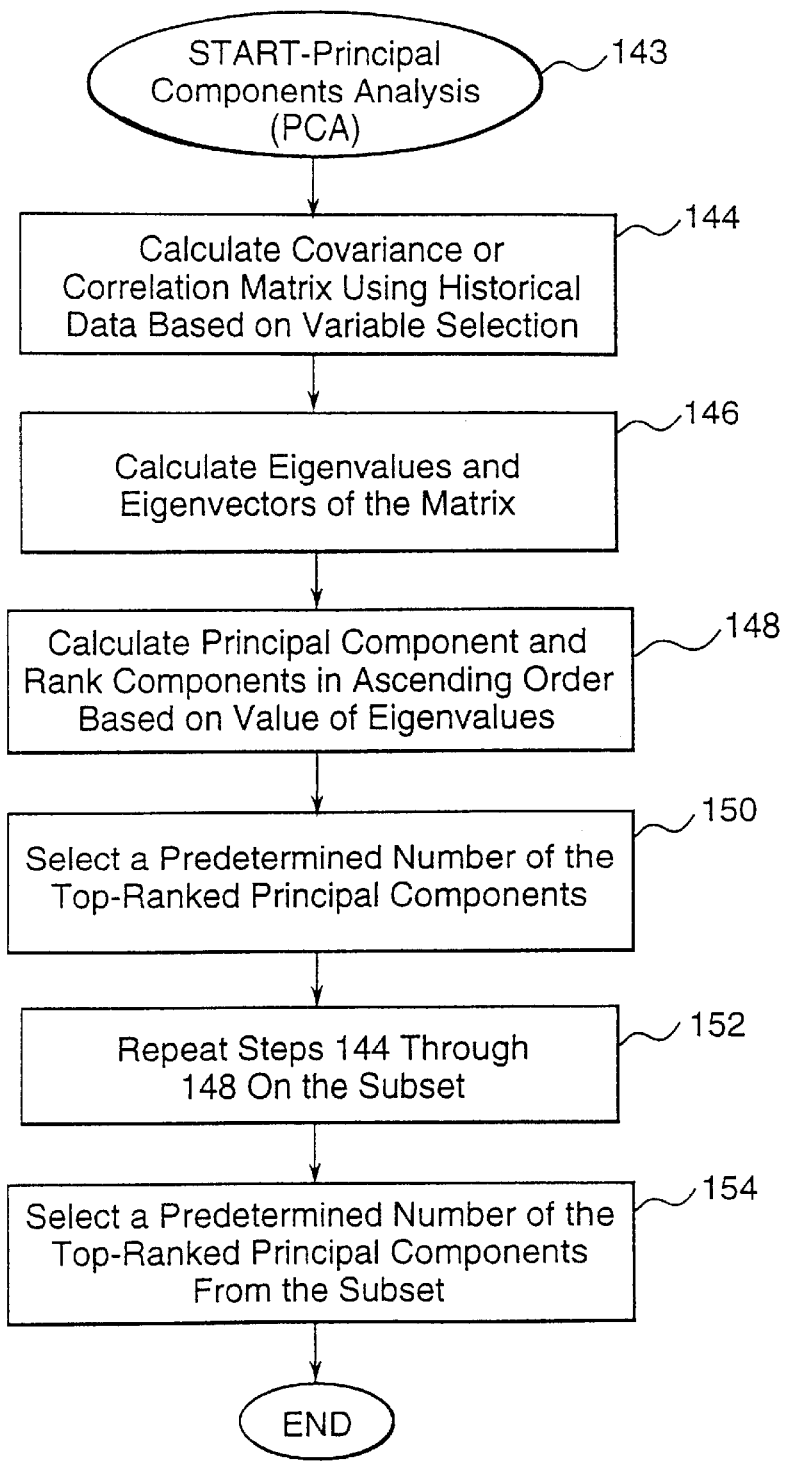
FIG. 12 is a flow chart setting forth the steps used in this invention to perform principal components analysis (PCA) on the acquired historical data.

Referring to FIG. 12, there are a number of steps in principal components transformation:
   Calculation of a covariance or correlation matrix using the selected variables data at 144.
   Calculation of the eigenvalues and eigenvectors of the matrix at 146.
   Calculation of principal components and ranking of the principal components based on eigenvalues at 148, where the eigenvalues are an indication of variability in each eigenvector direction.

In building a model, therefore, the number of variables identified by the variable selection techniques can be reduced to a predetermined number of principal components. In the preferred embodiment, the first three principal components are utilized to build the model—a reduction in dimensionality from 31 readings to three principal components. Note that the above reduction comes from both variable selection and PCA.

In the preferred embodiment, two experiments are performed for the computation of the principal components. First, all 31 variables from the variable selection technique are utilized, including their associated break positive data, and the coefficients obtained in the PCA are identified. Then, a smaller subset of a predetermined number of variables (16 in this case) are selected at 150 by eliminating variables (15 in this case) whose coefficients were too small to be significant. Then another PCA is performed at 152 utilizing this smaller subset. This result is summarized in Table 2.

TABLE 2

Principal components analysis of 16 break positive sensors.

| Principal Components | Eigenvalue | Proportion | Cumulative |
|---|---|---|---|
| PRIN1 | 14.42 | 90.14% | 90.14% |
| PRIN2 | 0.49 | 3.07% | 93.20% |
| PRIN3 | 0.32 | 1.98% | 95.19% |
| PRIN4 | 0.25 | 1.57% | 96.76% |
| PRIN5 | 0.18 | 1.10% | 97.85% |
| PRIN6 | 0.08 | 0.51% | 98.37% |
| PRIN7 | 0.06 | 0.38% | 98.75% |
| PRIN8 | 0.05 | 0.34% | 99.09% |
| PRIN9 | 0.04 | 0.24% | 99.33% |
| PRIN10 | 0.03 | 0.22% | 99.55% |
| PRIN11 | 0.03 | 0.16% | 99.71% |
| PRIN12 | 0.02 | 0.11% | 99.82% |
| PRIN13 | 0.01 | 0.08% | 99.90% |
| PRIN14 | 0.01 | 0.05% | 99.95% |
| PRIN15 | 0.01 | 0.04% | 100.00% |
| PRIN16 | 0.00 | 0.00% | 100.00% |

From the first row of Table 2, in the preferred embodiment, the first principal component explains 90% of the total sample variance. Further, the first six principal components explain over 98% of the total sample variance. Thus, a predetermined number of the top-ranked principal components, and their associated data, are selected at 154. Consequently, in the preferred embodiment, it is determined that sample variation may be summarized by the first three principal components and that a reduction in the data from 16 variables to three principal components is reasonable. As one skilled in the art will realize, any predetermined number of principal components may be selected, depending on the number of variables desired and the amount of variance desired to be explained by the variables.

Figure 13:
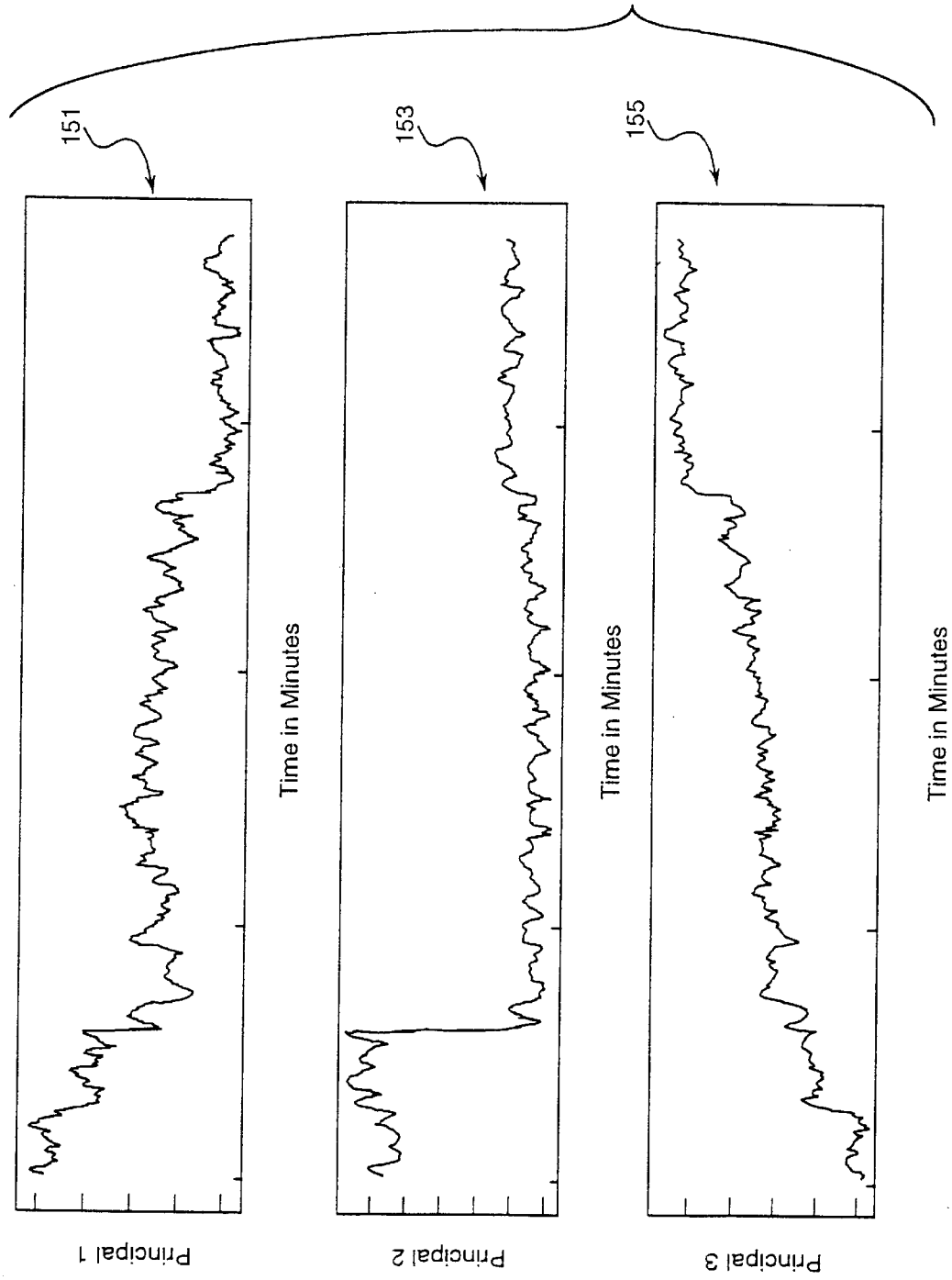
FIG. 13 is a graph for one preferred embodiment of the time-series data of the first three principal components of a representative break trajectory.

As a result of the principal component analysis, the time-series of the, first three principal components for each break trajectory may be generated. FIG. 13 represents a plot of the time-series of the first three principal components 151, 153 and 155 for a representative break trajectory.

Once the principal components are identified, then value transformation techniques 80 are applied to the principal components data in order to build the predictive model. The main purpose of value transformation is to remove noise, reduce data size by compression, and smooth the resulting time-series to identify and highlight their general patterns (i.e., velocity, acceleration, etc.). This goal is achieved by using typical signal-processing algorithms, such as a median filter and a rectangular filter.

Figure 14:
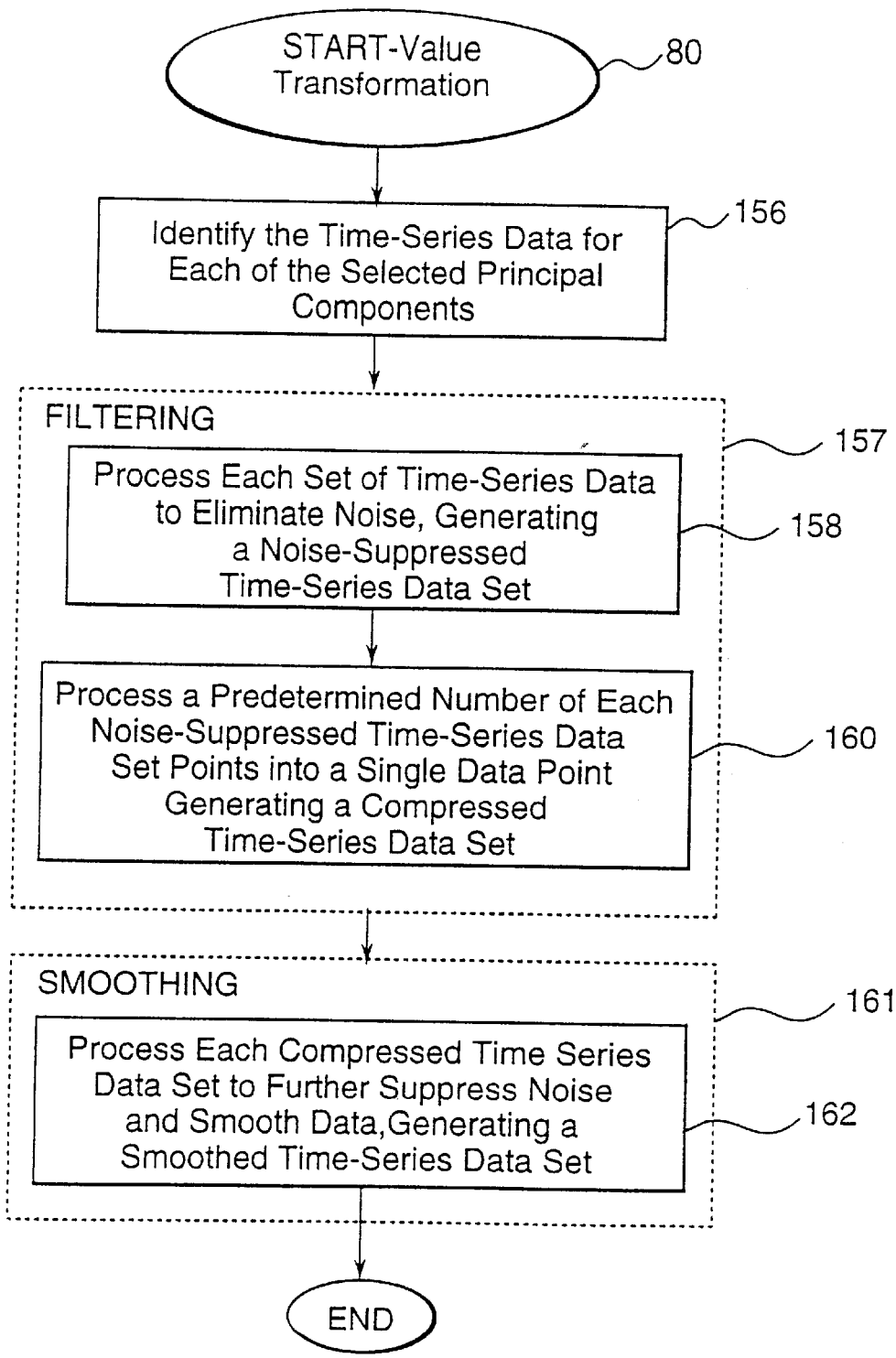
FIG. 14 is a flow chart setting forth the steps used in this invention to perform value transformation of the time-series data for the selected principal components.
Figure 15:
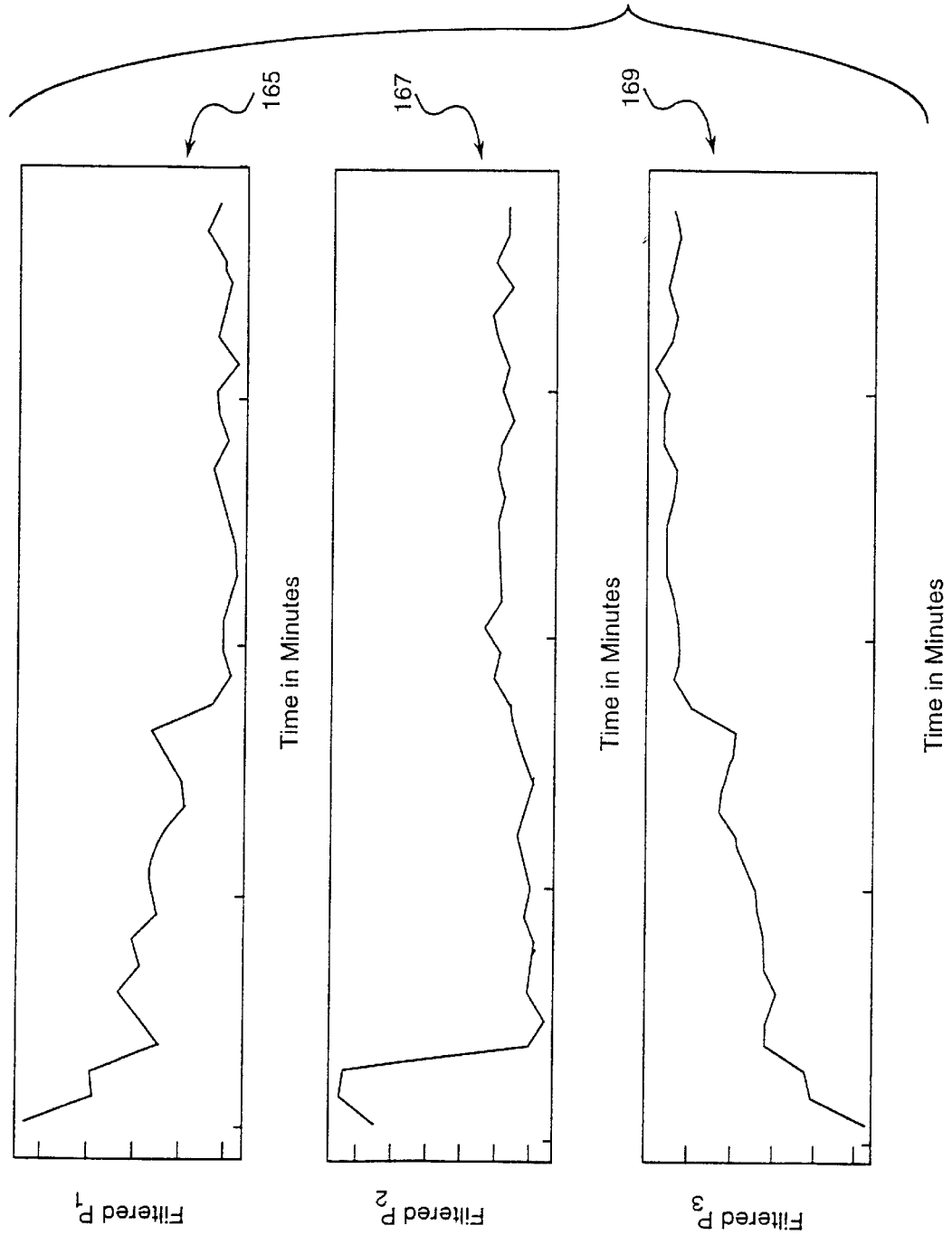
FIG. 15 is a graph for one preferred embodiment of the filtered time-series data of the first three principal components of FIG. 13.
Figure 16:
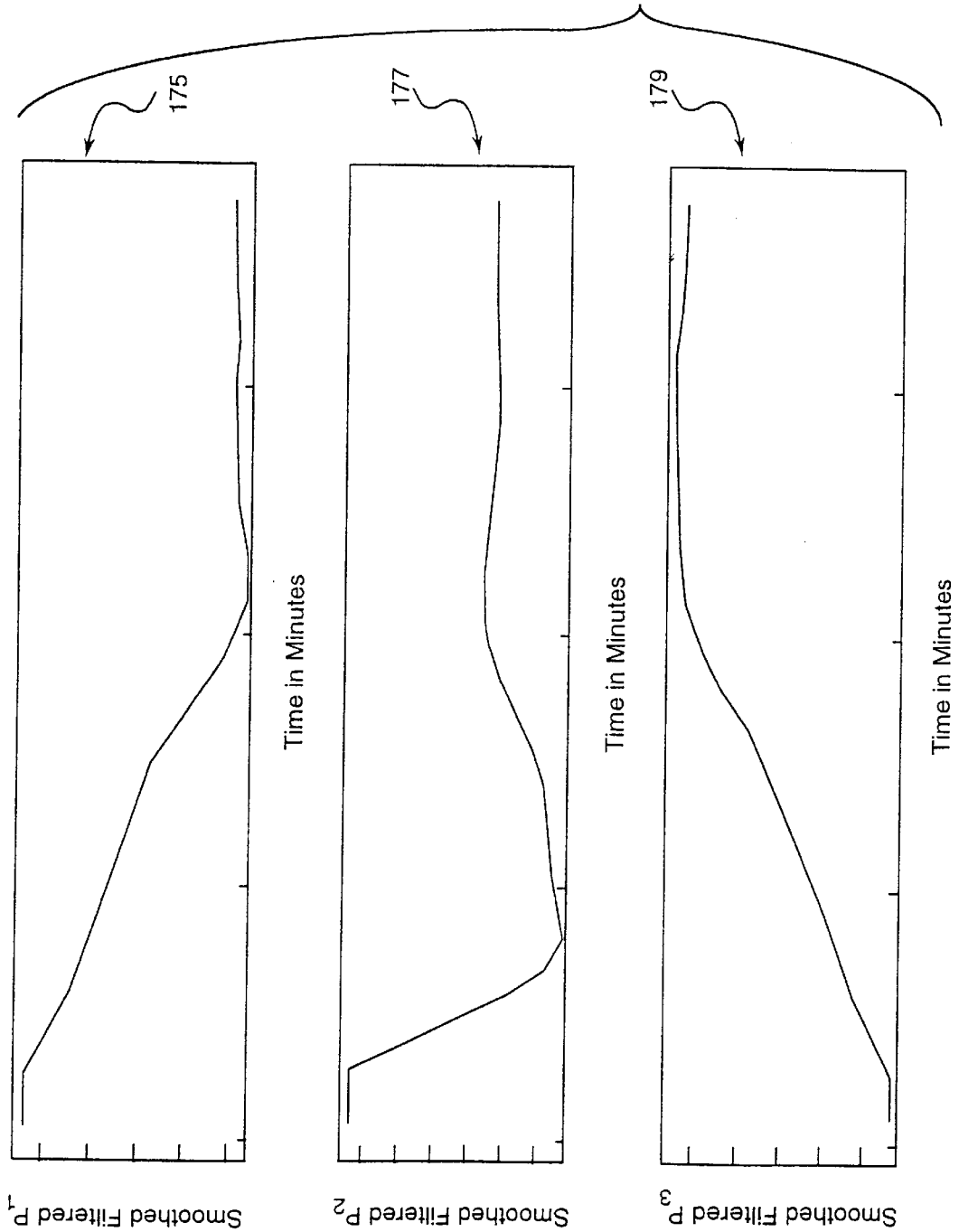
FIG. 16 is a graph for one preferred embodiment of the smoothed, filtered time-series data of the first three principal components of FIG. 15.

Referring to FIG. 14, the time-series data for each selected principal component is identified at 156. Each set of time-series data is suppressed to form a noise-suppressed time-series data set at 158. Then each noise-suppressed time-series data is compressed to form a compressed, suppressed time-series data set at 160. For example, a value transformation using a median filter serves two purposes—it filters out noises and compresses data. This results in summarizing a block of data into a single, representative point. FIG. 15 shows the filtered time-series plot of the three principal components 165, 167 and 169 of the representative break trajectory of FIG. 13. Note that the window size of the median filter is three. Further, additional filters may be applied to smooth the data to form a smoothed, compressed, suppressed time-series data set at 162. For example, a rectangular moving filter may be applied across the sequence of the three principal components in steps of one. This results in smoothing the data and canceling out sensor noises. FIG. 16 shows the smoothed, filtered time-series plot of the three principal components 175, 177 and 179 of the representative break trajectory of FIGS. 13 and 15. Note that the window size of the rectangular filter is five.

The next step in the model building process is model generation. Its main purpose is to provide a prediction of the web break sensitivity of the paper machine. To accomplish this goal, a set of features are extracted at 163 (FIG. 17) from the first three principal components. Then, a CART technique 173 (FIG. 18) is utilized that partitions the feature space into regions labeled Break or Non-break, which indicate high and low break sensitivity, respectively. Thus, the model generation results in a model that produces a break sensitivity indicator based on the incoming data to predict web breakage.

Figure 17:
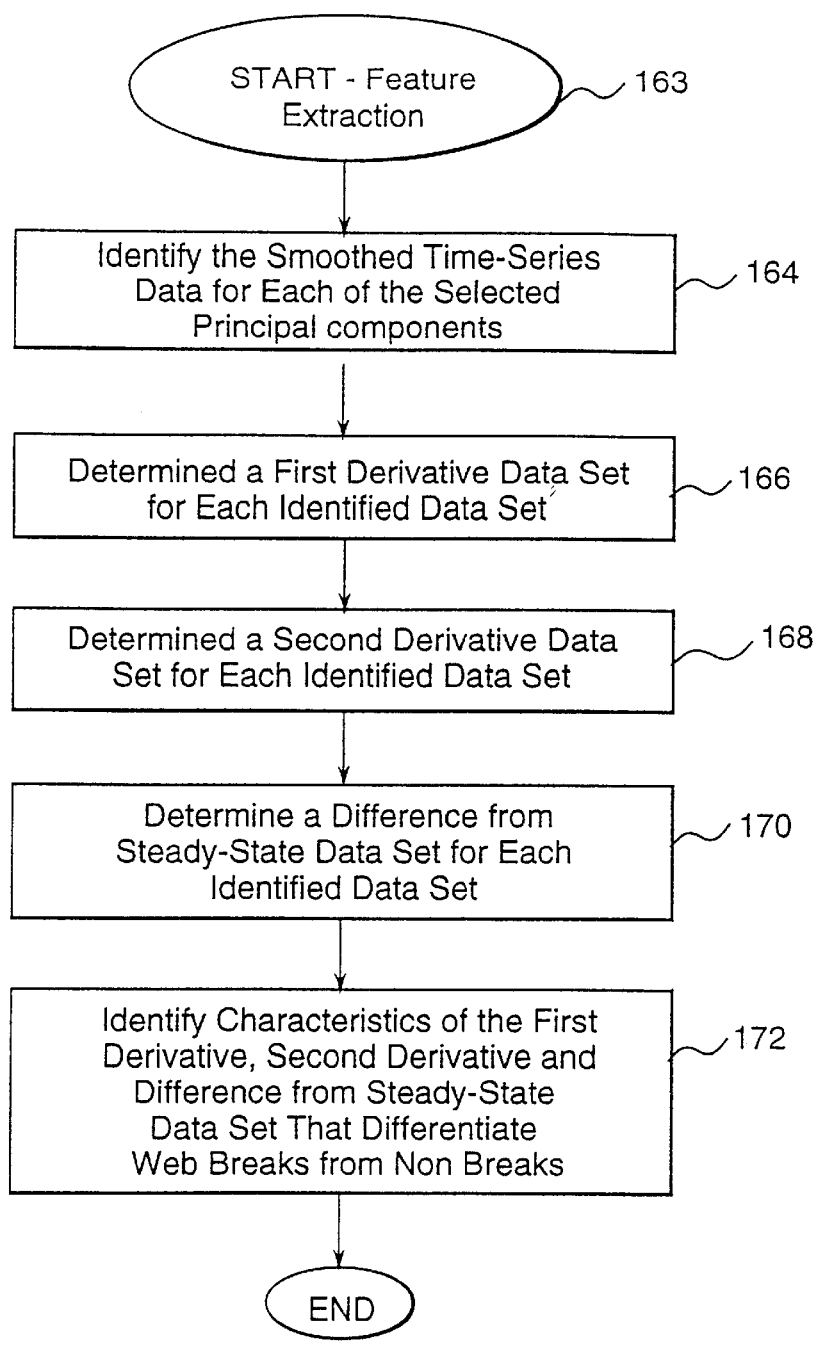
FIG. 17 is a flow chart setting forth the steps used in this invention to perform feature extraction on the smoothed, filtered time-series data for each selected principal component.

Referring to FIG. 17, the feature extraction involves extracting a predetermined number of features from the smooth, filtered break trajectory of each principal component. In particular, the smoothed time-series data set for each of the selected principal components is identified at 164. Then, a predetermined number of features indicative of web break sensitivity are determined for each principal component. In the preferred embodiment, for example, three features from each principal component were determined to be useful in predicting web breakage:

First derivative at 166—this is in essence the difference between two consecutive points (velocity);

Second derivative at 168—this is in essence the difference between two consecutive first derivatives (acceleration); and Difference from steady-state at 170—the difference between current sensor readings and that of a steady-state, where the steady-state is defined as the average of the first three points after filtering and smoothing.

Figure 18:
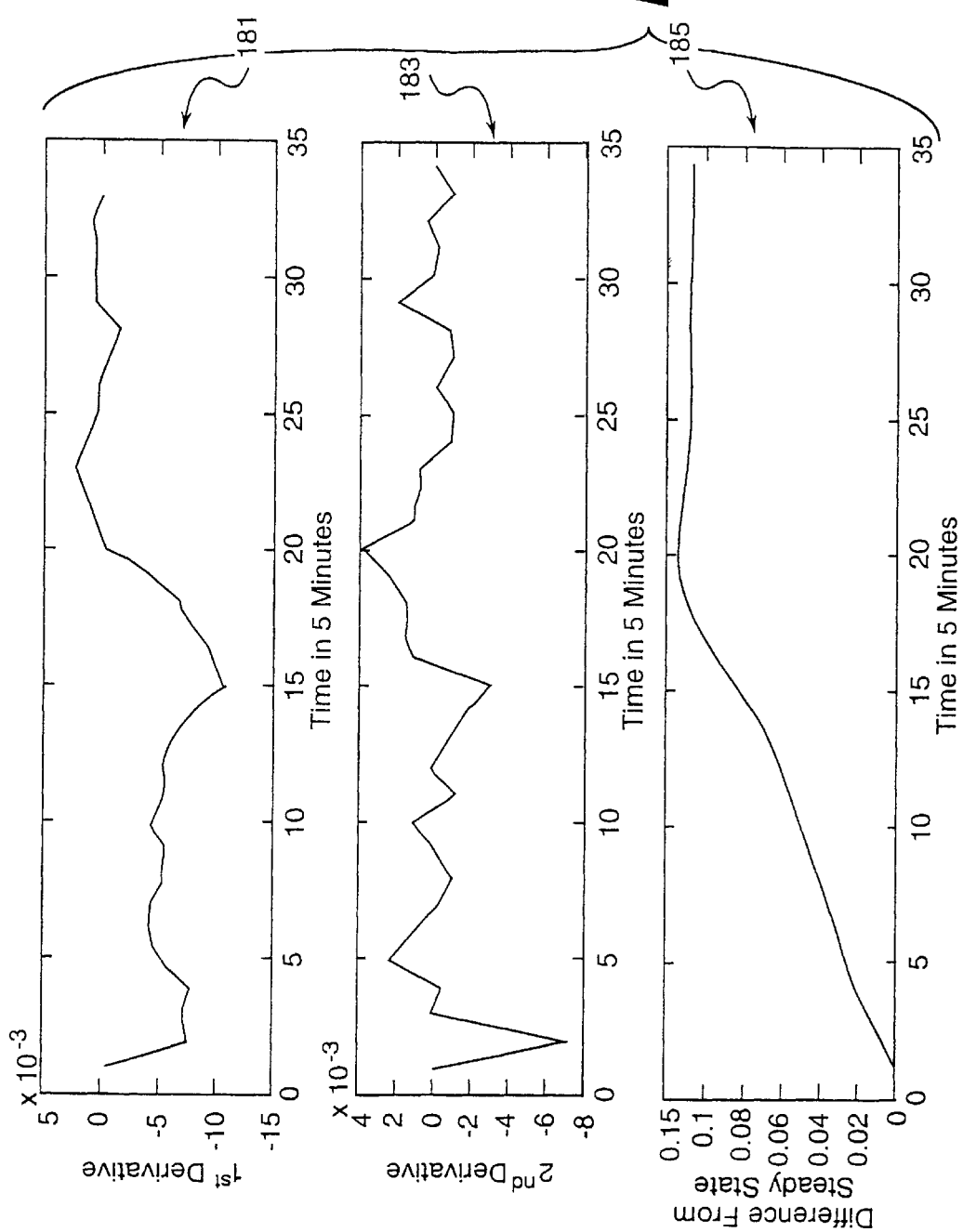
FIG. 18 is a graph for one preferred embodiment of the time-series data of the three features of the selected principal component of FIG. 16.

For example, referring to FIG. 18, the features of the break trajectory of the first principal component of the preferred embodiment are shown. The X-axis represents time from the start of the operation to a web break. As mentioned above, the idea of feature extraction is to extract the features with discriminating power in differentiating web breaks from non-breaks. In this example, both features one (first derivative 181) and two (second derivative 183) display the characteristic that their values approach zero when the status of the operation approaches a web break. In addition, the value of feature three (difference from steady-state 185) increases when the status approaches a web break. Thus, the characteristics of the features of the principal components that differentiate web breaks from non-breaks are identified at 172.

For prediction purposes, it is desirable to establish a predetermined time period prior to a break in which to establish an alert that a break is imminent. For example, using a 180 minute break trajectory window, the data set may be evenly divided and the data points closest to the break point may be identified with the imminent break. As a result, the model labels the data points within the 90 minute time period prior to the break as "Break" and all the rest of the points as "Non-Break" (not shown in the figure). Note that the time scale in FIG. 18 is in five minute frames, and thus 90 minutes corresponds to the last 18 data points.

Next, CART, the statistical algorithm of classification trees as discussed above, is used in combination with bagging, or sampling with replacement, as a predictive model for web break sensitivity. CART classifies the status of the paper-making operation as "Break" and "Non-Break" depending on the value of the principal components and their extracted features. CART is an inductive reasoning tool that infers unknown classification rules from the break sensitivity data. This inference process generally involves receiving a set of inputs, such as the break sensitivity data. The inductive reasoning tool then attempts to derive a set of rules or a classification tree that relate the inputs to a target output, such as the web break status. This approach generates a static partition of the feature space by defining regions with a high probability of break (status=Break) separate from regions with low probability of break (status=Non-Break). Thus, this method provides a coarse indicator of an impending web break.

Bagging or bootstrap aggregation is a technique that averages a given (statistical) procedure over many samples (bootstrap sample) to reduce its variance. Bootstrap algorithms are applied to generate bootstrap samples. As such, the predictive model is an aggregated or averaged predictive model developed from many independent predictive models based on sampling of the data set. Although random sampling with replacement is preferred, other sampling methods may be utilized. An intuitive view of bagging is that the prediction is improved if the entire population of data is utilized. In reality, it is not possible to have access to the entire population. Thus bootstrapping, or sampling with replacement, is used to approximate the underlying population.

Mathematically, bagging is explained as follows. Bagging improves the accuracy of estimators of functions $\theta(x)$ of a multivariate argument $$x = \{x_1, \ldots, x_p\} \text{ from data } \{y_i, x_i\}_1^n \quad \hat{\theta}(x) = \arg\max_{\theta(x) \in \theta} L(\theta(x)). \quad (1)$$

Here $\theta$ represents a function class representable by the estimator, such as neural networks, decision trees and preferably classification and regression trees in this case. In other words, equation 1 represents predictive modeling by maximizing likelihood. The objective function $L(\theta(x))$ is a data based estimate of the expected value of some function, such as log-likelihood or other negative loss functions $l(y,\theta)$, $$L(\theta(x)) = \frac{1}{n}\sum_{i=1}^{n} l(y_i, \theta(x_i)). \quad (2)$$

In other words, equation 2 involves averaging over the sample data. "Bagging" the estimator $\hat{\theta}$ involves repeating equations (1) and (2) many times, $B_1$ each time on a different randomly drawn subsample $S_b\{y_i, x_i\}_1^n$ of the data. In other words, bootstrapping by sampling with replacement. This induces a series of estimates $$\hat{\theta}_b(x) = \arg\max_{\theta(x)\in\phi} \frac{1}{n}\sum_{i\in Sb} l(y_i, \theta(x_i)), b\in\{1, \ldots, B\}.$$

The resulting "bagged" estimate is taken to be their average, $$\hat{\theta}_B(x) = \frac{1}{B}\sum_{b=1}^{B} \hat{\theta}_B(x).$$

Alternatively, a geometric interpretation of bagging is as follows:

---

$\hat{\theta}_B(X) = \arg\max_{\theta(x)\in\Theta} J(\theta(X))$ $J(\bullet)$ is an objective function in an optimization procedure $J(\bullet) \approx$ parabolic in shape + cubic-polynomial bumps + quartic-degree bumps + higher orders in Taylor-Expansion Bagging
   Reducing the variability of the nonlinear component by replacing it with an estimate of its expected value
   Leaving the linear part unaffected
   Achieves this variability reduction by averaging over bootstrap samples for the same procedure
   Most successful for highly nonlinear estimators like decision trees/neural networks

---

Figure 19:
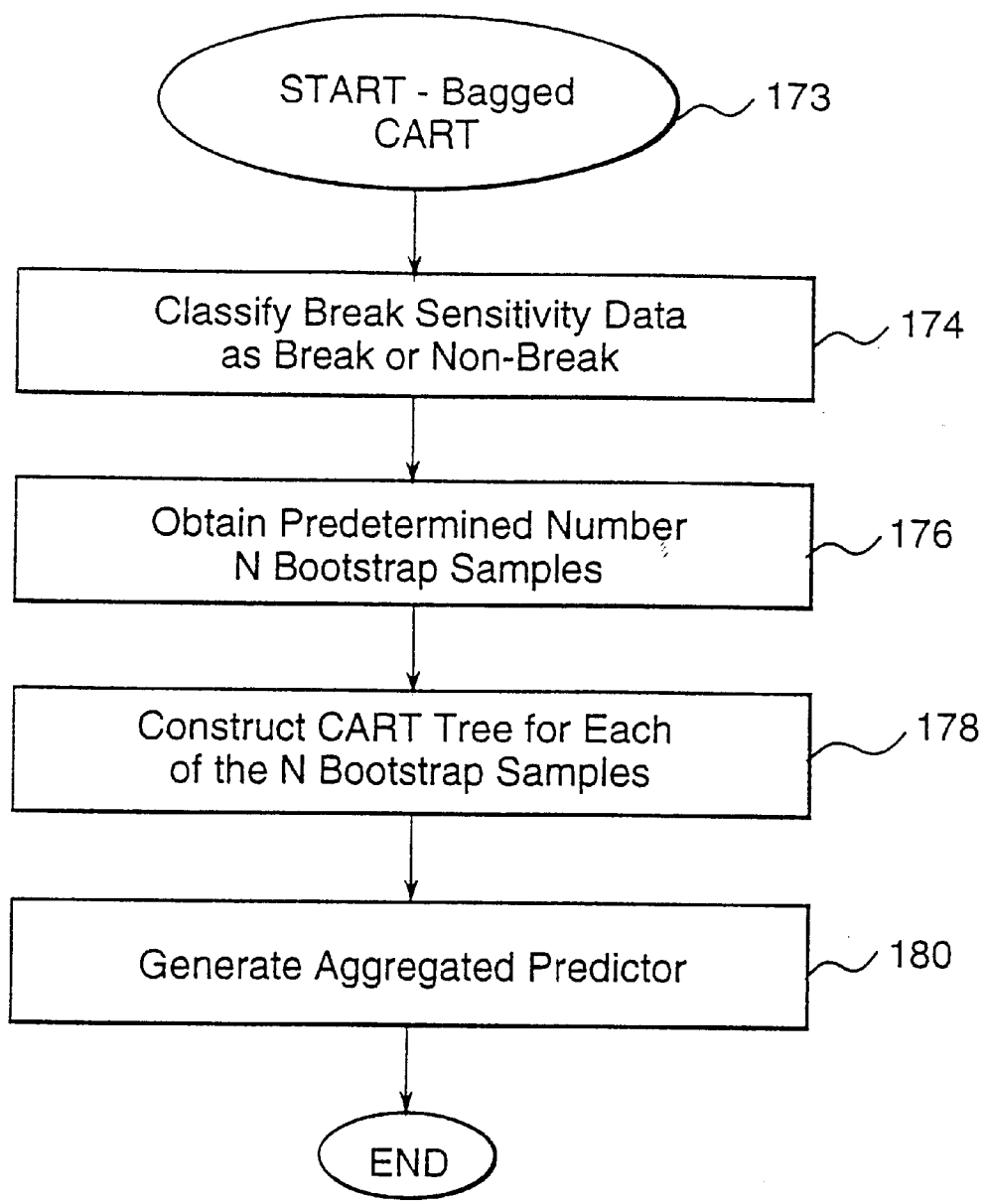
FIG. 19 is a flow chart setting forth the steps used in this invention to generate an aggregate classification and regression tree predictive model.

In generating the predictive model, referring to FIG. 19, the principal components and their extracted features are classified as break or non-break at 174. Then, a predetermined number N of bootstrap samples are obtained from the principal components and their extracted features at 176. For example, each of the bootstrap samples comprises a data set equal in size to the original data set of the principal components and their extracted features, obtained by random sampling with replacement of the original data set. A CART tree is then constructed for each of the bootstrap samples at 178. In the preferred embodiment, each CART tree is grown until the size of any terminal node is less than 1/n of the original data set, where n is an integer usually within the range of about 10 to about 20. An aggregated predictor is then generated by running the test data set through the N CART trees and averaging the result at 180. Therefore, the aggregated predictor or bagged CART model evaluates the break sensitivity data from the paper machine, i.e. the principal components and their extracted features, to predict a break sensitivity, i.e. break or non-break.

A list of results from bagging CART, in one preferred embodiment, are set forth below in Table 3.

TABLE 3

Result of Bagged CART

|  | Training Misclassification | Test Misclassification | # of Bootstrap Samples |
|---|---|---|---|
| CART | 0.219 | 0.267 | 0 |
| Bagged CART (1) | 0.195 | 0.269 | 11 |
| Bagged CART (2) | 0.184 | 0.262 | 20 |
| Bagged CART (3) | 0.183 | 0.248 | 60 |

Training (700 data points)
Test (165 data points)

Based on these results, the bagged CART with 60 bootstrap samples reduces the misclassification rate by more than 16% and 7% for the training and test data, respectively, compared to CART without bagging. Typically, between 20 and 100 bootstrap samples may be utilized. One skilled in the art will realize, however, that the predetermined number N of bootstrap samples may vary widely, depending on the desired accuracy of prediction, the available computing resources, the specific size of the data sets, etc.

Figure 20:
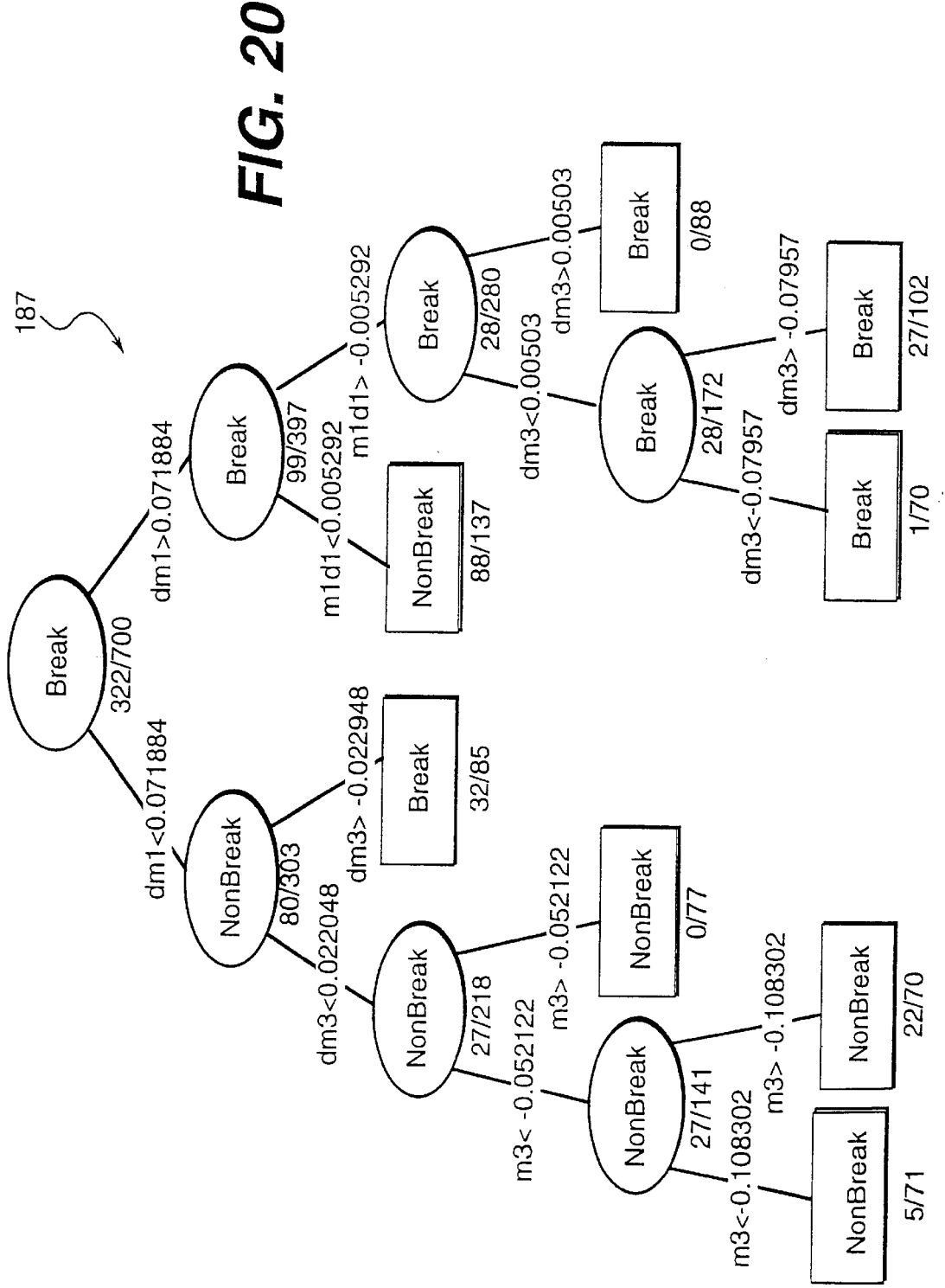
FIG. 20 is a graph representing one preferred embodiment of one of N bagged CART models for wet-end breakage prediction in paper mills.

FIG. 20 shows one representative tree 187 out of the N trees generated during the output of the bagged CART analysis of web breakage prediction for the preferred embodiment. This tree 187 is utilized by the break predictor 47 in determining the web break prediction. The labels in FIG. 20 are defined in Table 3.

TABLE 3

Label definitions in FIG. 20.

| Label | Definition |
|---|---|
| dm1 | Difference from steady state in principal one |
| dm3 | Difference from steady state in principal three |
| m1d1 | First derivative in principal one |
| m3 | Principal three |

A set of decision rules for diagnostics, can be generated from each tree resulting from the bagged CART. An example of some of the rules that are derived from one representative CART tree are listed below. This list is illustrative of some of the possible rules that may be derived in this invention and is not exhaustive of all of the possible set of rules that can be generated. For instance, one rule is:

IF (dm1<0.071664) AND (dm3>0.022046)
   THEN (status is Break)

The interpretation of the rule is that the status of papermaking operation is "Break" if principal one is close to its steady state and principal three is away from its steady state. The rule misclassification error was 32/85=37.6%.

For example, another rule is:

IF (dm1>0.071664) AND (m1d1>−0.005292)
     AND (dm3>0.00503)
   THEN (status is Break)

The interpretation of the rule is that the status of the paper-making operation is "Break" if principal one is away from its steady state, the first derivative of principal one is away from its steady state, and principal three is away from its steady state. The rule misclassification error was 0/88=0%.

The following is a list of software tools that may be utilized for the processes of the present invention:

1 Data scrubbing—the Excel™ software program or the MATLAB™ software program (to read files); SAS™ software program (to scrub data files)

2 Data segmentation—SAS™ software program
3 Variable selection—SAS™ software program; Splus CART™ software program; Excel™ software program or MATLAB™ software program (to visualize variables over time)
4 Principal Components Analysis (PCA)—SAS™ software program
5 Filtering—MATLAB™ software program
6 Smoothing—MATLAB™ software program
7 Feature extraction—MATLAB™ software program
8 Classification and regression trees—Splus CART™ software program
9 Bagging—Splus CART™ software program.

As one skilled in the art will realize, other similar software may be utilized to produce similar results, such as the Splus™ program, the C4.5™ program and the Knowledge Seeker™ program.

Although this invention has been described with reference to predicting web breaks in the wet-end section of the paper machine, this invention is not limited thereto. In particular, this invention can be used to predict web breaks in other sections of the paper machine, such as the dry-end section and the press section.

It is therefore apparent that there has been provided in accordance with the present invention, a system and method for predicting a web break in a paper machine that fully satisfy the aims, advantages and objectives hereinbefore set forth. The invention has been described with reference to several embodiments; however, it will be appreciated that variations and modifications can be effected by a person of ordinary skill in the art without departing from the scope of the invention.

What is claimed is:

1. A system for predicting a web break in a paper machine located about a paper mill, comprising:
    a paper mill database containing a plurality of measurements obtained from the paper mill, each of the plurality of measurements relating to a predetermined paper machine variable;
    a processor for processing each of the plurality of measurements into break sensitivity data; and
    an aggregated break predictor responsive to the processor for predicting a web break sensitivity within the paper machine from the plurality of processed measurements.

2. The system according to claim 1, wherein the aggregated break predictor comprises an inductive reasoning tool.

3. The system according to claim 1, wherein the aggregated break predictor comprises an average model from a plurality of predictive models each derived from a historical web breakage data set.

4. The system according to claim 3, wherein each of the plurality of predictive models comprise data randomly sampled from the historical web breakage data set.

5. The system according to claim 3, wherein each of the plurality of predictive models comprise data randomly sampled with replacement from the historical web breakage data set.

6. The system according to claim 1, wherein the aggregated break predictor comprises an aggregated classification and regression tree model.

7. The system according to claim 6, wherein the classification and regression tree model comprises a bootstrap aggregation model.

8. The system according to claim 1, wherein the break sensitivity data comprise time-based transformations of the plurality of measurements.

9. The system according to claim 1, wherein the break sensitivity data comprise principal components in determining web breakage from the plurality of measurements.

10. The system according to claim 8, wherein the break sensitivity data further comprise a principal component first derivative value, a principal component second derivative value and a principal component difference from steady-state value.

11. The system according to claim 1, wherein the plurality of measurements contained in the paper mill database are generated from various processes occurring within the paper mill.

12. The system according to claim 1, wherein the paper mill database comprises a raw materials database, a preprocess database, a paper machine database, an operation shift database and a maintenance schedule database.

13. A system for predicting a web break in a paper machine located about a paper mill, comprising:
    a paper mill database containing a plurality of measurements obtained from the paper mill, each of the plurality of measurements relating to a predetermined paper machine variable;
    a processor for processing each of the plurality of measurements into break sensitivity data; and
    an aggregated break predictor responsive to the processor for predicting a web break sensitivity within the paper machine from the plurality of processed measurements, wherein the aggregated break predictor comprises an aggregated classification and regression tree model.

14. The system according to claim 13, wherein the aggregated classification and regression tree model comprises an average of a plurality of predictive models each derived from a historical web breakage data set.

15. The system according to claim 14, wherein each of the plurality of predictive models comprise data randomly sampled from the historical web breakage data set.

16. The system according to claim 14, wherein each of the plurality of predictive models comprise data randomly sampled with replacement from the historical web breakage data set.

17. The system according to claim 13, wherein the classification and regression tree model comprises a bootstrap aggregation model.

18. The system according to claim 17, wherein the break sensitivity data comprise time-based transformations of the plurality of measurements.

19. The system according to claim 18, wherein the break sensitivity data comprise principal components in determining web breakage from the plurality of measurements.

20. The system according to claim 19, wherein the break sensitivity data further comprise a principal component first derivative value, a principal component second derivative value and a principal component difference from steady-state value.

21. The system according to claim 13, wherein the plurality of measurements contained in the paper mill database are generated from various processes occurring within the paper mill.

22. The system according to claim 13, wherein the paper mill database comprises a raw materials database, a preprocess database, a paper machine database, an operation shift database and a maintenance schedule database.

23. A method for predicting a web break in a paper machine located about a paper mill, comprising:
    obtaining a plurality of measurements from the paper mill, each of the plurality of measurements relating to a predetermined paper machine variable;

processing each of the plurality of measurements into break sensitivity data; and predicting a web break sensitivity within the paper machine from the plurality of processed measurements using an aggregated break predictor.

24. The method according to claim 23, wherein predicting the web break sensitivity comprises processing the break sensitivity data using an aggregated inductive reasoning tool.

25. The method according to claim 23, wherein predicting the web break sensitivity comprises processing the break sensitivity data using an aggregated classification and regression tree model formed using a bootstrap algorithm.

26. The method according to claim 23, wherein the aggregated break predictor comprises an average of a plurality of predictive models each derived from a historical web breakage data set.

27. The method according to claim 26, wherein each of the plurality of predictive models comprise data randomly sampled from the historical web breakage data set.

28. The system according to claim 26, wherein each of the plurality of predictive models comprise data randomly sampled with replacement from the historical web breakage data set.

29. The method according to claim 25, further comprising training the aggregated classification and regression tree model with historical web break data to learn how to predict web break sensitivity.

30. The method according to claim 29, further comprising testing the trained aggregated classification and regression tree model with the historical break data to test how well the model predicts web break sensitivity.

31. The method according to claim 29, wherein the training comprises preprocessing the historical web break data.

32. The method according to claim 31, wherein the preprocessing comprises:

reducing the quantity of the historical web break data;

reducing the number of variables contained in the historical web break data;

transforming the values of the historical web break data;

extracting features that affect web break sensitivity from the historical web break data;

applying a bagging algorithm to the extracted features; and generating the classification and regression tree model to predict a web break sensitivity from the bagged extracted features.

33. The method according to claim 32, wherein reducing the quantity of historical web break data includes selecting data associated with a web break having a predetermined cause.

34. The method according to claim 32, wherein reducing the quantity of historical web break data includes selecting data within a predetermined time period of a web break.

35. The method according to claim 32, further comprising segmenting the historical web break data.

36. The method according to claim 35, wherein segmenting the data includes selecting data associated with a predetermined paper grade.

37. The method according to claim 35, wherein segmenting the historical web break data includes dividing the data into break positive data and break negative data.

38. The method according to claim 37, wherein dividing the data into break positive data includes segmenting the break positive data by time-series analysis.

39. The method according to claim 32, wherein reducing the number of variables includes processing the data utilizing a technique selected from the group consisting of knowledge engineering, visualization, classification and regression trees and logistic regression.

40. The method according to claim 32, wherein reducing the number of variables includes processing the data utilizing principal components analysis.

41. The method according to claim 32, wherein transforming the values of the historical web break data includes smoothing or filtering the data.

42. The method according to claim 23, wherein the obtaining of the plurality of measurements comprises receiving measurements generated from various processes occurring within the paper mill.

43. A method for predicting a web break in paper machine located about a paper mill, comprising:

obtaining a plurality of measurements from the paper mill, each of the plurality of measurements relating to a predetermined paper machine variable;

processing each of the plurality of measurements into break sensitivity data; and predicting a web break sensitivity within the paper machine from the plurality of processed measurements using a break predictor comprising an average of a plurality of predictive models each derived from a historical web breakage data set.

44. The method according to claim 43, wherein the break predictor, processes the break sensitivity data using an aggregated inductive reasoning tool.

45. The method according to claim 44, wherein each of the plurality of predictive models comprise data randomly sampled from the historical web breakage data set.

46. The system according to claim 45, wherein each of the plurality of predictive models comprise data randomly sampled with replacement from the historical web breakage data set.

47. The method according to claim 46, wherein predicting the web break sensitivity comprises processing the break sensitivity data using an aggregated classification and regression tree model formed using a bootstrap algorithm.

48. The method according to claim 47, further comprising training the aggregated classification and regression tree model with historical web break data to learn how to predict web break sensitivity.

49. The method according to claim 48, further comprising testing the trained aggregated classification and regression tree model with the historical break data to test how well the model predicts web break sensitivity.

50. The method according to claim 43, wherein the obtaining of the plurality of measurements comprises receiving measurements generated from various processes occurring within the paper mill.

* * * * *